United States Patent [19]
Thanavala et al.

[11] Patent Number: 5,856,087
[45] Date of Patent: *Jan. 5, 1999

[54] METHOD FOR DETECTING IMMUNE RESPONSE TO HEPATITIS B

[75] Inventors: Yasmin Thanavala; Arvind Thakur, both of Williamsville, N.Y.

[73] Assignees: Health Research, Inc., Buffalo, N.Y.; University College London, London, England

[*] Notice: The term of this patent shall not extend beyond the expiration date of Pat. No. 5,531,990.

[21] Appl. No.: 948,762

[22] Filed: Oct. 10, 1997

Related U.S. Application Data

[63] Continuation of Ser. No. 589,011, Jan. 19, 1996, Pat. No. 5,744,135, which is a continuation of Ser. No. 167,336, Dec. 15, 1993, Pat. No. 5,531,990.

[51] Int. Cl.$^6$ .............................. C12Q 1/70; C12P 21/06; A61K 38/00; A61K 38/04
[52] U.S. Cl. ............................... 435/5; 435/69.3; 514/14; 530/326; 530/328
[58] Field of Search ..................... 435/5, 69.3; 514/14; 530/326, 328

[56] References Cited

U.S. PATENT DOCUMENTS

| 4,778,761 | 10/1988 | Miyanohara et al. | 435/320 |
| 4,803,164 | 2/1989 | Hitzeman et al. | 435/68 |
| 5,531,990 | 7/1996 | Thanavala et al. | 424/131.1 |
| 5,744,135 | 4/1998 | Thanavala et al. | 424/131.1 |

OTHER PUBLICATIONS

Wands et al., "Identification and Transmission of Hepatitis B virus–related variants", Proc. Natl. Acad. Sci. USA, vol. 83, pp. 6608–6612, Sep. 1986.

"HBsAG Positive Reactivity in Man Not Due to Hepatitis B Virus", The Lancet, Dec. 12, 1987.

Neurath et al., "Toleration of Amino Acid Substitutions within Hepatitis B Virus Envelope Protein Epitopes Established by Peptide Replacement Set Analysis. I. Region S(139–147)" Peptide Res. vol. 3, No. 3 (1990).

Lai et al., "Hepatitis B virus DNA in the Serum of Sardinian Blood Donors Negative for the Hepatitis B Surface Antigen", Blood, Jan. 1989, 73(1).

Carman et al., "Vaccine–induced Escape Mutant of Hepatitis B Virus", The Lancet, vol. 336, pp. 325–329 (Aug. 1990).

Egea et al., "The Cellular Basis for Lack of Antibody Response to Hepatitis B Vaccine in Humans", Exp. Med., vol. 173, pp. 531–538 (Mar. 1991).

Cupps et al., "In Vitro Immune Responses to Hapatitis B Surface Antigens S and preS2 during Acute Infection by Hepatitis B Virus in Humans", The Journal of Infectious Diseases, 161, pp. 412–419 (1990).

Cupps et al., "In Vitro Immune Responses to Hepatitis B Surface Antigen (Pre–S2 and S) Following Remote Infection by Hepatitis B Virus in Humans", Journal of Clinical Immunology, vol. 9, No. 3, (1989).

Jin et al., "Human T cell Response to the Surface Antigen of Hepatitis B Virus (HBsAg)", Journal of Experimental Medicine, vol. 168, pp. 293–306 (1988).

Jin et al., "An Oligoclonal Human T–Cell Line Specific for HBsAg is Restricted to MHC Class I Antigens and Responds to Soluble Antigen and to Endogenous HBsAg" Viral Hepatitis and Liver Disease, pp. 678–683 (1988).

Chang et al., "In Vitro Response to HBsAg of Peripheral Blood Lymphocytes from Recipients of Hepatitis B Vaccine", Hepatology, vol. 4, No. 5, pp. 824–829 (1984).

Celis et al., Recognition of Hepatitis B Surface Antigen by Human T Lymphocytes, The Journal of Immunology, vol. 140, pp. 1808–1815, No. 6 (1988).

Celis et al., "Hepatitis B Virus–Reactive Human T Lymphocyte Clones: Antigen Specificity and Helper Function for Antibody Synthesis", The Journal of Immunol. vol. 132, No. 3, (1984).

Primary Examiner—Susan A. Loring
Attorney, Agent, or Firm—Michael L. Dunn

[57] ABSTRACT

The invention comprises an anti-idiotypic antibody designated 2F10 and permitted variants thereof, which have antigenic properties similar to the group specific "a" determinant of human hepatitis B surface antigen HBsAg and have at least partial but not complete homology with such surface antigen. The invention further comprises a peptide having a chain comprising the amino acid residues Ala Val Tyr Tyr Cys Thr Arg Gly Tyr His Gly Ser Ser Leu Tyr and permited variants thereof, which, like 2F10, have antigenic properties similar to the group specific "a" determinant of human hepatitis B surface antigen HBsAg and have at least partial, but not complete, homology with said surface antigen. The amino acid sequence is found in and forms a part of 2F10. The shorter peptide chain comprising the amino acid residues Gly Tyr His Gly Ser Ser Leu Tyr and permited variants thereof, also have antigenic properties similar to the group specific "a" determinant of human hepatitis B surface antigen HBsAg and have at least partial, but not complete, homology with said surface antigen.

2 Claims, 7 Drawing Sheets

```
                                       124                                     134
HBsAg                                  Cys Thr Thr Pro Ala Gln Gly Asn Ser Met Phe
                                        |   |       .       :   |   .   |   :   :
2F10  (H:88)       Ala Val Tyr Tyr Cys Thr Arg Gly Tyr His Gly Ser Ser Leu Tyr  (H:100b)
                    :       :   :   |   |   :   .       .   |   .
HBsAg              Pro Ser Cys Cys Cys Thr Lys Pro Thr Asp Gly Asn
                   135                                         146
```

METHOD FOR DETECTING IMMUNE RESPONSE TO HEPATITIS B

This is a Continuation of Application Ser. No. 08/589,011, filed on Jan. 19, 1996, now U.S. Pat. No. 5,744,135, which is a Continuation of Application Ser. No. 08/167,336, filed on Dec. 15, 1993, now U.S. Pat. No. 5,531,990.

This work is sponsored by the National Institute of Health Grant Nos. AI-24328 and AI-27976. The U.S. Government may have certain rights in this invention.

BRIEF DESCRIPTION OF THE INVENTION

The invention comprises an anti-idiotypic antibody designated 2F10 and permitted variants thereof, which have antigenic properties similar to the group specific "a" determinant of human hepatitis B surface antigen HBsAg and have at least partial but not complete homology with such surface antigen.

The invention further comprises a peptide having a sequence comprising the amino acid residues Ala Val Tyr Tyr Cys Thr Arg Gly Tyr His Gly Ser Ser Leu Tyr and permited variants thereof, which, like 2F10, have antigenic properties similar to the group specific "a" determinant of human hepatitis B surface antigen HBsAg and have at least partial, but not complete, homology with said surface antigen. The amino acid sequence is found in and forms a part of 2F10.

The shorter peptide chain comprising the amino acid residues Gly Tyr His Gly Ser Ser Leu Tyr and permited variants thereof, also have antigenic properties similar to the group specific "a" determinant of human hepatitis B surface antigen HBsAg and have at least partial, but not complete, homology with said surface antigen.

The invention also comprises a hybridoma cell line designated 2F10 which produces the antibody 2F10 as above described.

The monoclonal anti-idiotypic antibody 2F10 has significant utility as discussed below.

The antibody or the above sub-peptides thereof have the ability to provoke in vitro responses in CD4$^+$ T cells purified from the blood of human Hepatitis B virus (HBV) carriers as well as from those who have developed an immune response due to vaccination or exposure to the virus. The antibody and the above peptides therefore can act to detect individuals who have an immune response to hepatitis B. This is important to determine if vaccination has been effective and to determine if there is a developed T cell immunity through exposure which can eliminate the need for redundant immunization. Furthermore the ability to determine whether there is an immune response even though there has been no vaccination can be used as a screening tool to suggest further testing to decide whether a person is a carrier. Carriers have have not cleared the virus from their systems and therefore can transmit the disease and there is clear evidence that the incidence of hepatocellular carcinoma is greatly increased in such carriers. It is therefore important to detect such carriers for their own treatment as well as to prevent disease transmission.

It has also been established that immunization with the antibody is able to circumvent non-responsiveness in a mouse strain B10.M (H2$^f$) which has been characterized as a non-responder to the a determinant of hepatitis B surface antigen (HBsAg), i.e these mice, when injected with the above anti-idiotypic antibody or peptides make a specific (HBsAg) antibody response which was previously not obtainable. It has now additionally, and more importantly, been shown that T cells obtained from human vaccine non-responders also respond in vitro when stimulated with the above anti-idiotypic antibody and peptides even though they fail to respond to either HBaAg or synthetic peptides derived from it. It can therfore be expected that the antibody and peptides of the invention has significant potential as a vaccine that is able to raise a response in all immunized individuals.

In this context, the antibody and peptides of the invention make less costly vaccines possible thus permitting access to those individuals and countries where the prohibitive cost of present vaccines prevent its use.

It should be further understood that the anti-idiotypic antibody (anti-Id) and peptides of the invention provide valuable tools in the study of hepatitis since they mimic the antigenic properties of HBsAg yet are able to raise a response effective for HBsAg in circumstances where HBsAg itself is unable to do so.

BRIEF DESCRIPTION OF THE DRAWINGS

FIG. 1A shows response in BALB/c (H-2$^d$) mice. FIG. 1B shows response in SWR/J (H-2$^q$) and FIG. 1C shows response with B10.M (H-2$^f$). Results are expressed as OD 492:660 of the avearage of five mice per group at either a 1:20 dilution (SWR/j and BALB/c) or a 1:5 dilution (B10.M) of their sera.

FIGS. 3A–3D show determination of epitopes on anti-Id 2F10 mAb responsible for mimicking the a determinant of HBsAg. FIG. 3A shows a composite of SDS/PAGE with subsequent immunoblot analysis probed with $^{125}$I-labeled H3F5. Lanes: 1 and 2, mAbs 2F10 and 2C3 nonreduced; 3 and 4, mAbs 2F10 and 2C3 reduced. FIG. 3B shows a comparison of the region of deduced amino acid sequence of mAb 2F10 H chain showing partial homology with the HBsAg S-region amino acid sequence, –=identity, .=significant similarity, .=some similarity. The numbering of the S region amino acids is as described in Valenzuela et al, Nature, 280, 815–819. FIG. 3C shows a computer simulated model of mAb 2F10 Fv region depicting the H chain CDR3 residues H:96 to H:100b (white), other H- and L-chain CDRs (green) and framework regions (blue). FIG. 3D shows a graph of the solvent accessible surface (SAS) van der Waals area (VDW Å) of the CDRs was calculated according to the algorithm ACCESS as set out in Lee et al J. Mol. Biol. 55, 379–400. The SAS area of the H chain CDR3 is shown. Residues H:96Y-H100bY are highly exposed.

FIG. 4A shows a comparison of anti-HBsAg antibody responses elicited by immunization with rHBsAg-alum (●), anti-id 2F10 mAb (■), 2F10 15-mer peptide (Δ), or 2F10 15-mer peptide-KLH (▲). Results are expressed as OD 492:660 nm of the average of five mice per group at a 1:20 dilution. Sera from mice injected with unconjugated 2F10 15-mer peptide were assayed at a 1:2 dilution. FIG. 4B shows results of proliferation assays with purified T cells from mice primed in vivo with rHBsAg-alum (●), anti-id 2F10 mAb (■), or 2F10 15-mer peptide-KLH (▲). Cells were stimulated in triplicate cultures with the following in vitro stimuli: rHBsAg (0.5 µg per well), anti-id 2F10 mAb and control mAb (50 µg per well), 2F10 15-mer peptide and control peptide (0.25 µg per well), Con A (1 µg per well), or medium alone.

DETAILED DESCRIPTION OF THE INVENTION

Figure 1A:
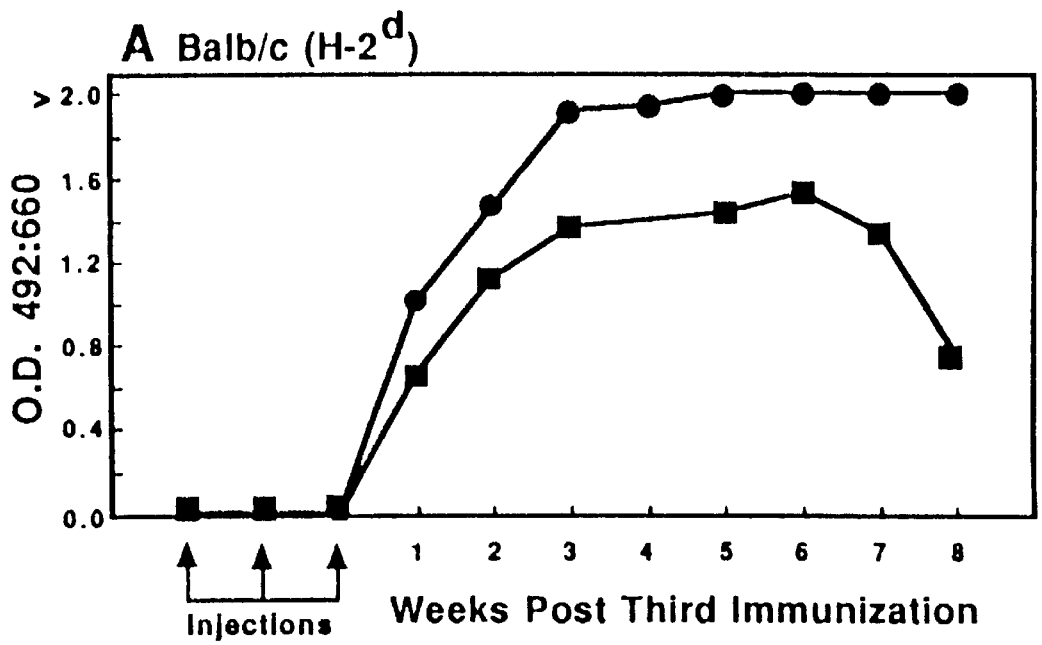
FIGS. 1A–1C are graphs showing a comparison of anti-HB's antibody responses elicited by immunization with anti-Id (■) of the invention or rHBsAg (•).

"Anti-idiotypic antibody" or "Ab2" as used herein means an antibody made against a first antibody. In the case of hepatitis B surface antigen, it is an antibody made against an antibody for the surface antigen.

"To have antigenic properties similar to the group specific 'a' determinant of human hepatitis B surface antigen HBsAg" means that an antibody raised against the antiidiotypic antibody will also be an antibody against HBsAg.

"To have at least partial but not complete homology with HBsAg" means that there is a correlation between peptide sequences in the anti-idiotypic antibody and at least one sequence present in HBsAg but there is not a complete correspondence. In a sequence of 11 amino acids there should be at least two amino acids which are identical and in the sme relative positions and there should be a number, i.e. at least two and preferably at least three amino acids, at corresponding positions, which are not identical but have similar reactivities. In general there should be fewer than 20 numerical percent of amino acids at the same relative positions which do not have at least some reactive site similarity.

"Permitted variant" as used herein means that an amino acid substitution may be made which does not have a significant negative impact on the similarity of antigenic properties when compared with HBsAg. In general the H100, H100a, and H100b amino acids, i.e. Ser Leu Tyr sequence in 2F10 and the above described peptides, or the equivalent thereof, should not be eliminated (see FIG. 3B). In addition the Glycine prior to the Ser Leu Try sequence should not be eliminated or substituted. For probable permitted variants reference may be had to Pride et al, Peptide Research, Vol 5, No.4, 217–226 and Neurath et al, Peptide Research, Vol 3, No. 3, 116–122.

Infection with human hepatitis B virus (HBV) results in a gamut of clinical symptoms ranging from minor flu-like symptoms to death. The wide spectrum of responses is believed to be accounted for by the host's immune response to the virus because HBV is not directly cytopathic for hepatocytes (Thomas, H. C. et al., Hepatology 2, 116S–121S (1982)). The specific serologic marker of HBV infection is the envelope protein, hepatitis B surface antigen (HBsAg), which contains three related proteins designated S, M (S plus pre-S2), and L(M plus pre-S1) . All of these proteins share the 226-amino acid sequence of the S protein (in this paper, HBsAg will refer to the S protein). HBsAg possesses a common group-specific a determinant and two sets of mutually exclusive subtype-specific determinants d/y and w/r. Because antibodies directed toward the a determinant confer protection against HBV infection, regardless of subtype (Szmuness, S. et al., N. Engl. J. Med., 307, 1481–1485 (1982)), any vaccine developed to prevent HBV infection should elicit immunity to the a determinant.

The immune network theory proposed by Jerne (Ann. Immunol. (Paris) 125C, 373–389 (1974)), predicts the appearance of several types of anti-idiotype (anti-id) antibodies during the immune response to a given antigen. The subset of "internal-image" anti-id antibodies (termed Ab2β) has been proposed to be anti-paratopic and to mimic the molecular features of the original antigen (Nisonoff, A. et al., Clin. Immunol. Immunopathol. 21, 397–406 (1981) and Roitt, I. M. et al., Immunol. Today 6, 265–267 (1985)). This working hypothesis is based on the concept that certain homologous or analogous molecular motifs of the anti-id sequence can mimic specific immunogenic epitopes of the infectious organism, thereby inducing a protective immune response (Nisonoff et al. and Roitt et al. supra). Such anti-id antibodies have been used in various experimental systems as surrogate vaccines against specific bacterial, viral, and parasitic organisms (for review, see Hiernaux, J. R., Infect. Immun. 56, 1407–1413 (1988) and Eichmann, K., et al., Crit. Rev. Immunol. 7, 93–227 (1987)).

Analogous to the situation with HIV, there is no imbred animal model for hepatitis B virus (HBV) infection and therefore most studies have evaluated HBV proteins as immunogens rather than as infectious agents. Extensive work by Milich, D. R., Immunol. Rev. 99:71 (1987), and others has established that the murine immune response to the group-specific a determinant of hepatitis B surface antigen (HBsAg) is H-2 restricted and shows a hierarchy of responsiveness at the B and T cell level. The hierarchy of the humoral response to HBsAg is as follows: high responders, $H\text{-}2^{q,d}$; intermediate responders, $H\text{-}2^{a}>H\text{-}2^{b}>H\text{-}2^{k}$; and nonresponders, $H\text{-}2^{s,f}$. The T cell proliferative response to HBsAg generally paralleled the same H-2 restriction observed for the humoral response.

For the study of immune responses to HBV, we produced anti-Ids against a mouse mAb, designated H3F5 (Tedder, R. S., et al., J. Hyg. 90:135 (1983)), (Id, Ab1), which recognizes the protective a determinant epitope on HBsAg. The fusion of spleen cells obtained from BALB/c mice immunized with H3F5 resulted in six monoclonal anti-Ids.

All the anti-id antibodies inhibited the binding of HBsAg to the H3F5 id; however, only two of these anti-ids (2F10 and 4D4) were tentatively classified as internal-image anti-id antibodies by described criteria (Thanavala, Y. T., et al., Immunology 55, 197–204 (1985)) and recognized an interspecies crossreactive Id, as demonstrated by the reaction of these hybridomas with polyclonal anti-HBs sera from a variety of species (Thanavala, Y. M., et al. Immunology, 55:197 (1985) and Thanavala, Y. M., et al. J. Immunol. Methods. 83:227 (1985)). Since the a determinant on HBsAg is important in conferring protection (Szmuness, S., et al., N. Engl. J. Med. 307:1481 (1982)), we therefore wanted to determine whether our anti-Ids carried an internal image of the a determinant. To test this, anti-HBs sera (ad or ay specific) were adsorbed with HBsAg ad or ay. Only adsorption of antibodies against the a determinant abolished reactivity of the polyclonal sera with the anti-Ids (Thanavala, supra.) 2F10 and 4D4 were therefore tentatively classified as "internal image" anti-Ids (Ab2β), and one of these anti-Ids (2F10) was further studied to determine if it could mimic HBsAg and generate specific B and T cell responses. Immunization with the anti-Id 2F10 could elicit HBsAg-specific B and T cell responses that, unlike the antigen it mimics, are not restricted by a known HBsAg non-responder haplotype.

In accordance with this invention, anti-id 2F10 elicits, in several mouse strains, anti-HBsAg antibodies and prime T cells in vivo that can subsequently be stimulated in vitro by HBsAg. 2F10 can also stimulate in vitro CD4+ T cells from human donors that had been primed in vivo to HBsAg as a result of vaccination or HBV infection (Pride, M., et al., in Idiotype Networks in Biology and Medicine, eds. Osterhaus, A. & Uytdehaag, F. (Elsevier Science, Amsterdam), pp. 263–270 (1990)).

To identify the epitopes responsible for this observed mimicry, we began an extensive structural analysis of anti-id 2F10. We show that the mimicry of HBsAg by anti-id 2F10 is associated with a 15-amino acid sequence on its heavy-chain (H chain) hypervariable region. This sequence is partially homologous with a determinant epitopes of HBsAg, and a synthetic peptide corresponding to this sequence can duplicate the B- and T-cell stipulatory activity of the intact anti-id and HBsAg. More particularly, an 8-amino acid sequence was found which mimics HBsAg.

Materials and Methods

Animals. BALB/c mice (H-$2^d$) were obtained from West Seneca Labs (West Seneca, N.Y.). B10.M(H-$2^f$) and SWR (H-$2^q$) were obtained from The Jackson Laboratory (Bar Harbor, Me.). Wild mice, *Mus spretus*, were a kind gift from Dr. Verne Chapman (Roswell Park Cancer Institute). All mice were female and 6–8 weeks old at the start of the study.

In Vivo and in Vitro Stimuli. H3F5 is mouse mAb (IgG2b) that is specific for the protective a determinant epitope S-(139–147) on HBsAg (Tedder, R. S., et al., J. Hyg. 90, 135–142 (1983)) and is the id that anti-id 2F10 recognizes. 2F10 is a mouse internal-image anti-id mAb of the IgG1 subclass that mimics the group-specific a determinant of HBsAg (Thanavala, Y. T., et al., Immunology 55, 197–204 (1985)). mAbs 2F10 and H3F5 were purified from ascites fluid by 45% ammonium sulfate precipitation and then passage over a protein A column.

2F10 Fab was prepared by digestion of the purified anti-Id with immobilized papain followed by a protein A-Sepharose column to remove Fc fragments and any undigested IgG, according to manufacturer's directions (Pierce Chemical Co., Rockford, Ill.). Separation of anti-Id 2F10 into H and L chains was performed essentially as described elsewhere (Hudson, L., et al., Practical Immunology, Blackwell Scientific Publications, London, 118 pp, (1980)), except dithiothreitol was used as the reducing agent. The murine mAb 2C3 (specific for the hapten phthalate) has the same subclass as 2F10 and was used as a control throughout this study (kindly provided by Dr. S. Ghosh, Indiana State University, Terre Haute, Ind.). HBsAg is the outer envelope protein of the hepatitis B virus. rHBsAg and rHBsAg-alum devoid of pre-S proteins were generously provided by Dr. W. F. Miller (Merck, Sharp and Dohme Research Laboratories, Westpoint, Pa.). A nine-amino acid synthetic peptide (CTKPTDGNC) that represents a partial analogue of the group-specific a determinant located in the S region (139–147) of HBsAg (Bhatnager, P. K., et al., Proc. Natl. Acad. Sci. USA, 79:4400 (1982)) was used as a positive control in antigen processing experiments. The peptide was synthesized as a COOH-terminal amide, and the purity (>80%) was assessed by HPLC using a Vydac C-18 column (Multiple Peptide Systems, San Diego, Calif.) and was conjugated to keyhole limpet hemocyanin (KLH) via glutaraldehyde. The control peptide used in these experiments was either a variant of the S(139–147) peptide (CTKPŚD ŔNC; this peptide was previously shown to abrogate T cell proliferative responses to murine T cells that were primed with rHBsAg (Neurath, A. R., et al., I. Region S(139–147). Pept. Res. 3:116 (1990)) or a 15-amino acid peptide from a sequence of yellow fever virus (GAMRVTKDTNDNNLY).

Induction of Anti-HBs Antibodies. Mice (five/group) were immunized intraperitoneally on days 0, 7, and 14 with either rHBsAg, 2F10 anti-Id, or control antibody 2C3. rHBsAg was administered as an alum-adsorbed precipitate at a dose of 0.5μ/animal per injection. 2F10 anti-Id or control mAb was administered at 100 μg/animal per injection in CFA, IFA, and saline, respectively. Mice were bled retro-orbitally and the sera evaluated for anti-HBs-specific antibodies using a commercially available ELISA kit (AUSAB; Abbott Diagnostic Laboratories, Chicago, Ill.).

Isotype Distribution of the Anti-HBs Response. The isotype distribution of the anti-HBs response was determined using the Mouse Typer sub-isotyping kit (Bio-Rad Laboratories, Richmond, Calif.). Sera were diluted in PBS-0.05% Tween 20 and incubated on HBsAg-coated beads for 2 h. The beads were washed and a 1:2 dilution of rabbit anti-mouse subclass-specific antiserum was added for 1 hour. The beads were washed again and a 1:3,000 dilution of goat anti-rabbit horseradish peroxidase conjugate was added. After 1 hour, the beads were washed and developed in a peroxidase substrate solution (2,2'-amino-di[3-ethylbenzthiazoline sulfonate] and $H_2O_2$) for 30 minutes and results read on an automated EIA reader at 405 nm. The entire assay was performed at room temperature and every wash step consisted of five washes in PBS-Tween 20.

In Vitro Proliferation of Mouse Lymph Node T Cells. Mice (five/group) were immunized in the hind foot pads with either rHBsAg, anti-Id 2F10, or control monoclonal 2C3. Amount of antigen administered and schedule of immunization are the same as described above for the induction of anti-HBs antibodies. It may seem at first that our method of immunization for the induction of T cell responses is quite unorthodox (immunizing three times in the footpad vs. a single injection). We, however, only use 0.5 μg of rHBsAg per injection. This is substantially below the doses that are reported in the literature, where a single injection of 16 μg of HBsAg was administered and T cells collected 8–10 d later (Milich, D. R., et al., J. Immunol. 134:4194 (1985) and Milich, D. R., et al., J. Immunol. 134:4203 (1985)). 1 wk after the third injection the animals were killed and the popliteal lymph nodes were collected, teased apart, and the cells washed twice in RPMI 1640 supplemented with 2 mM L-glutamine, 100 U/ml penicillin, 100 μg/ml streptomycin, 50 μg/ml gentamicin, 0.2 mM nonessential amino acids, 11 μg/ml sodium pyruvate, 0.02M Hepes, and $5\times10^{-5}$ 2-ME (incomplete media), and once in complete media (incomplete media supplemented with 10% heat-inactivated FCS). T cell enrichment was performed at $10^8$ cells/0.6 g of packed nylon wool (Cellular Products, Buffalo, N.Y.). After enrichment, T cells were >97% pure as measured by staining with anti-Thy-1.2 antibody conjugated to FITC. The enriched T cells were adjusted to a concentration of $2.5\times10^5$ cells/well. 100 μl of cells was plated in 96-well flat-bottomed plates along with $5\times10^5$ irradiated syngeneic spleen cells as a source of APC. Appropriate concentrations of the different stimuli diluted in complete media (100 μl/well) were added to the cells in triplicate cultures. The stimuli were: rHBsAg (0.1 or 0.5 μg/well), 2F10 anti-Id and isotype control antibody (20 or 50 μg/well), synthetic peptide S(139-147) and control peptide (0.05 or 0.10 μg/well), Con A (1μ/well), or media alone. The cells were then cultured for 120 h in a 5.5% $CO_2$ incubator at 37° C. [$^3$H]TdR (1 μCi/well) was added to each well 18 h before the end of the culture period. The cells were harvested onto glass fiber filters using an automatic cell harvester (Scatron, Sterling, Va.). Proliferation, as measured by [$^3$H]TdR incorporation, was determined by liquid scintillation spectroscopy. Results are expressed as the mean cpm of [$^3$H]TdR incorporation of triplicate wells.

MHC Class II Restriction. To determine the MHC class II restriction in our system, we treated BALB/c (H-$2^d$) APC with mAbs MK-D6 or 34-1-4S, which are specific for I-A$^d$ and I-E$^d$, respectively. The MK-D6 and 34-1-4S cell lines were obtained from American Type Culture Collection (Rockville, Md.). $2\times10^7$ APC were incubated with 500 μl of either MK-D6 or 34-1-4S culture supernatant for 1 h at 4° C. with shaking. The cells were then washed three times in incomplete media. These APC were immediately used in in vitro T cell experiments as described previously.

Chloroquine and Paraformaldehyde Treatment of APC. In experiments directed towards studying the role of antigen processing, spleen cells (as a source of APC) were treated essentially according to the procedure of Kovac and Schwartz (J. Immunol. 134:3233 (1985)). $3\times10^7$ APC were incubated for 20 min with 2 ml of either 0.3M chloroquine or 0.5% (wt/vol) paraformaldehyde. The cells treated with chloroquine were washed four times in incomplete media and the cells treated with paraformaldehyde were washed five times in cold complete media. After this treatment, the APC were set up in in vitro T cell experiments as described above.

Gel Electrophoresis and Inmunoblotting. One-dimensional, discontinuous SDS/12% PAGE analysis (Mini-Protean II, Bio-Rad) as described by Laemmli (Nature (London) 227, 680–633, (1970)), was done on mAb 2F10 and control mAb 2C3 under reducing and nonreducing conditions. After electrophoresis, gels were prepared for immunoblotting and transferred electrophoretically from SDS gels to nitrocellulose paper (Towbin, H., et al., Proc. Natl. Acad. Sci. USA 76, 4350–4354 (1970)). The blot was probed with $^{125}$I-labeled H3F5 (id) (100,000 cpm/ml) for 2 hr, washed, and exposed to Kodak XAR-5 film with a Cronex intensification screen for 16–18 hr at −70° C.

Primer Extension and sequencing of mAb 2F10. Primer extension and sequencing of mAb 2F10 RNA was done essentially as described by Geliebter (Focus 9, 5–8 (1987)) by using the primer 5'-CTCACTGGATGGTGGGAAGATGGATACAGT-3' for the κ chain and the primer 5'-CAGGGGCCAGTGGATAGAC-3' for γl H chain. The sequence information was analyzed by the IBI/Pustell DNA sequence-analysis system of Pustell and Kafatos (Nucleic Acids Res. 12, 643–655 (1984)). For comparing mAb 2F10 light-chain (L) and H-chain amino acid sequences with the HBsAg amino acid sequence, we used the GAP algorithm of Needleman and Wunsch (J. Mol. Biol. 48, 443–453 (1970)).

Modeling of mAb 2F10. Computer-assisted modeling of the Fv region involved interactive graphics modeling based on canonical structures (Chothia, C. et al., J. Mol. Biol. 196, 901–917 (1987) and Chothia, C. et al., Nature (London) 342, 877–883 (1989)); the parent structures (REI, HyHEL-5, McPC603) used for the initial modeling have been solved by x-ray crystallography, and coordinates were obtained from the Brookhaven Protein Data Bank. Residue homology comparison, canonical scaffolding-building, energy minimization, conformational searches (Bruccoleri, R. E., et al., Nature (London) 335, 564–568 (1988)), and dynamics simulation techniques were all used to construct the model; use of these procedures has been described (Kussie, P. H., et al., J. Immunol. 146, 4248–4257 (1991)).

Induction of Anti-HBsAg Antibodies. BALB/c mice (five per group) were immunized i.p. on days 0, 7, and 14 with either rHBsAg, anti-id 2F10, or the 15-mer 2F10 peptide. rHBsAg was administered as an alum-adsorbed precipitate at a dose of 0.5 μg per injection. Anti-id 2F10, carrier-free 15-mer 2F10 peptide, or 15-mer 2F10 peptide coupled to KLH (52% peptide by weight) was administered at 100 μg per injection in complete Freund's adjuvant, incomplete Freund's adjuvant, and saline, respectively. Mice were bled retroorbitally before and after immunization, and the sera were evaluated for anti-HBsAg-specific antibodies using an ELISA kit (AUSAB-enzyme immunoassay).

In Vitro Proliferation of Mouse Lymph Node T Cells. Mice were immunized in the hind foot pads with either rHBsAg, anti-id 2F10, or the 15-mer 2F10 peptide-KLH. Amount of antigen and schedule of immunization are as described above. One week after the third injection, the animals were sacrificed, and the popliteal lymph nodes were collected and teased apart, the cells were purified as described elsewhere (Pride, M. W., et al., Peptide Res. 5, 217–226 (1992)). The enriched T cells were adjusted to a concentration of $2.5\times10^5$ cells per well. One hundred microliters of cells was plated in 96-well flat-bottomed plates along with $5\times10^5$ irradiated syngeneic spleen cells as a source of antigen-presenting cells. Stimuli diluted in complete medium were added to the cells in triplicate cultures. The stimuli are as follows: rHBsAg (0.5 μg per well), anti-id 2F10 and isotype control antibody (50 μg per well), 2F10 peptide and control peptide (0.25 μg per well), Con A (1 μg per well), or medium alone. The cells were then cultured for 120 hr as described (Pride, M. W., et al., Peptide Res. 5, 217–226 (1992)). Proliferation, as measured by [$^3$H] thymidine incorporation, was determined by liquid scintillation spectroscopy. Results are expressed as stimulation index.

Preparation of Human CD4$^+$ T cells. Peripheral blood mononuclear cells were prepared as described (Pride, M. W., et al., Peptide Res. 5, 217–226 (1992)). The technique of Mage et al. (J. Immunol. Methods 15, 47–56 (1977)) as modified by Wysocki and Sato (Proc. Natl. Acad. Sci. USA 75, 2844–2848 (1978)) was used to further purify the peripheral blood mononuclear cells into a CD4$^+$ subset by using the following antibodies: anti-Leu2a (mouse mAb that recognizes the CD8 cluster on human T cells; predominantly cytotoxic T/suppressor T cells), anti-21.147 (mouse mAb that recognizes the CD11b/18 cluster and has reactivity against suppressor T cells, natural killer cells, monocytes, and granulocytes) and anti-26.263 (mouse mAb that reacts with the β chain of HLA-DR, ODP, and -DQ). All panning reagents were provided by Robert Evans (Roswell Park Cancer Institute)

CD4$^+$ T-Cell Proliferation Assay. CD4$^+$ cells were cultured in 96-well flat-bottom plates along with autologous adherent cells (source of antigen-presenting cells) at a ratio of $2.5\times10^5$ CD4$^+$ cells/$1.25\times10^4$ adherent cells per well. All cells were cultured for 7 days in RPMI 1640 medium supplemented as above (no fetal calf serum), containing 10% heat-inactivated human AB$^+$ serum. Stimuli used are described above for mouse T-cell assays.

Figure 1B:
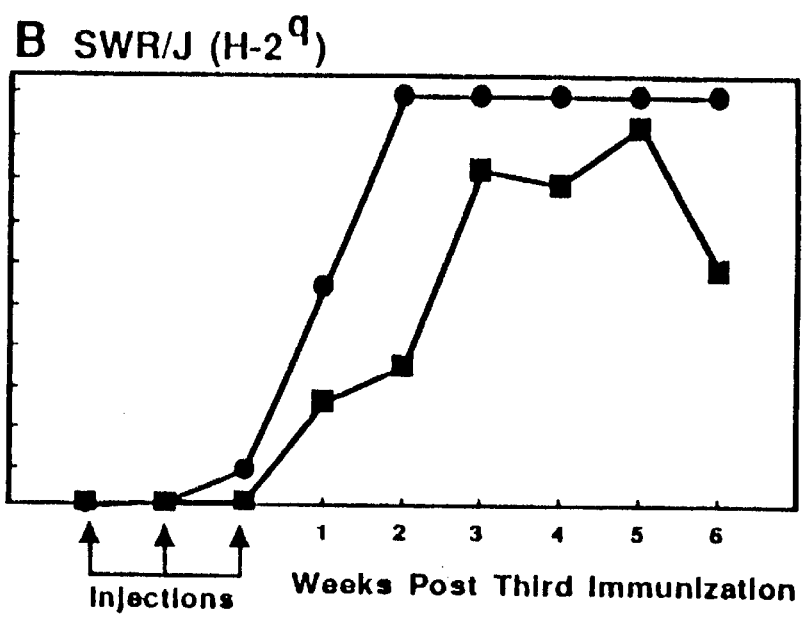
Figure 1C:
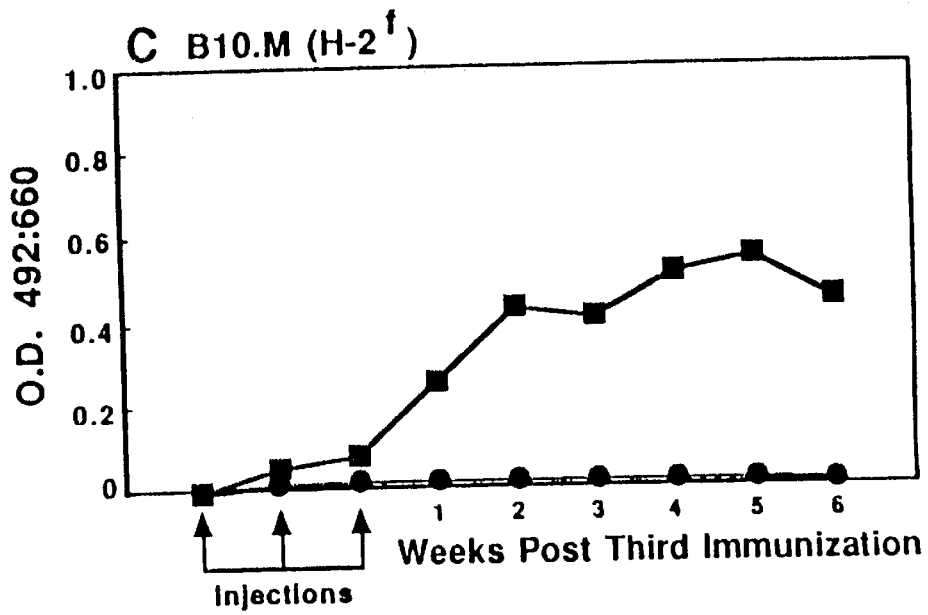

Anti-HBsAg Production by rHBsAg or Anti-Id. As shown in FIG. 1, A and B, both SWR/J (H-$2^q$) and BALB/c (H-$2^d$)

mice made a strong antibody response when injected with rHBsAg-alum, however, the B10.M strain (H-2$^f$) did not (FIG. 1 C), thus confirming earlier reports by other investigators on the classification of the B10.M strain as a nonresponder to HBsAg (Milich, D. R., et al., J. Immunol. 129:320 (1982)), The outbred wild mice, *M. spretus,* also made a strong anti-HBs response when injected with rHBsAg-alum (data not shown). Importantly, in all the above mouse strains (BALB/c SWR/J, B10.M, and *M. spretus*), an anti-HBs response was elicited when the mice were injected with the monoclonal internal image anti-Id 2F10 (FIG. 1, A–C). Thus, our anti-Id was successful in circumventing non-responsiveness to the α determinant of HBsAg in the B10.M mouse strain.

Isotype Distribution of Anti-HBs Responses. An analysis of the isotype distribution of the anti-HBs response showed that both anti-Id and rHBsAg induced responses in the BALB/c mice that were predominantly of the IgG1 subclass (Table 1) Additionally, the rHBsAg-immunized BALB/c mice produced a substantial amount of IgG2b and lesser amounts of IgG2a and IgM anti-HBs-specific antibodies. In sera from 2F10-immunized BALB/c mice collected at a later time point (3–5 wk after the third immunization), we also detected small amounts of IgG2b and IgM anti-HBs-specific antibodies. In contrast to the responses observed in BALB/c mice immunized with the anti-Id 2F10, B10.M mice produced predominantly anti-HBs antibodies of the IgG2b subclass and some IgG1 antibody.

In Vitro Proliferation Proliferation of HBsAg—or Anti-Id-primed T Cells. Purified T cells obtained from the popliteal lymph nodes of mice primed in vivo with rHBsAg were stimulated in vitro for 120 h with varying concentrations of anti-Id, control antibody, rHBsAg, a synthetic peptide corresponding to residues 139–147 of the S region protein of HBsAg, control peptide, or media along (Table 2). As previously shown by others, T cells from B10.M mice injected with HBsAg do not respond in vitro to HBsAg (Milich, D. R., et al., J. Immunol. 137:315 (1986)), and as seen in our experiments, these T cells also do not respond in vitro to the anti-Id. T cells obtained from the two other strains (BALB/c and SWR/J) primed with rHBsAg responded in vitro to both rHBsAg and anti-Id 2F10 (Table 2). Thus, the anti-Id is capable of efficiently stimulating in a specific manner T cells from rHBsAg-primed mice. Good proliferative responses were also observed in vitro with a synthetic nine-amino acid peptide (S[139–147]) that corresponds to a determinant residues of HBsAg.

In reciprocal experiments, T cells were obtained from mice primed in vivo with 2F10 anti-Id and stimulated in vitro with various stimuli. Table 3 shows that T cells obtained from BALB/c, SWR/J, B10.M, and *M. spretus* primed in vivo with anti-Id can respond in vitro to the anti-Id. More importantly, T cells primed in vivo by the anti-Id do proliferate in vitro to rHBsAg (except the B10.M strain). This result is significant if this anti-Id were to be used as an alternative vaccine to HBsAg. The lack of proliferation observed in cultures of T cells obtained from B10.M mice immunized with the anti-Id is not likely a reflection of an attenuated B cell response in these animals. Though the results of a longitudinal study of anti-HBsAg responses in three strains of mice (FIG. 1) suggests that B10.M mice make a weaker antibody response, we in fact have additional results (data not shown), wherein, B10.M mice immunized in the footpad with the anti-Id do make equivalent antibody response to those seen in BALB/c mice. However, even when using cells from these animals, no T cell response to rHBsAg could be elicited.

The nine-amino acid synthetic peptide S(139–147) was also able to elicit a response in vitro in BALB/c, SWR/J, and *M. spretus* (Table 3), again confirming the α determinant specificity of the response that out anti-Id is able to generate. The antigenic specificity of the proliferative responses shown in both Tables 2 and 3 is controlled by the lack of response in the absence of an in vitro stimulus (media alone), but more importantly, no response is observed in cultures stimulated with an isotype-matched control antibody or a control synthetic peptide. Additional specificity control was achieved by immunizing mice with our isotype-matched control antibody 2C3 and performing similar T cell assays as discussed earlier. The results in Table 4 show that no stimulation was observed with any in vitro stimuli except for the in vivo immunizing antibody 2C3.

To establish that our anti-Id was not stimulating these primed T cells nonspecifically by TCR crosslinking, we digested the anti-Id into either monovalent Fab fragments or separate H and L chains. As seen in Tables 2 and 3, both the anti-Id Fab fragments and H chains can stimulate T cells that were primed with either HBsAg or anti-Id. It is interesting to note that the H chain of the anti-Id stimulates these primed T cells very efficiently and probably accounts for most of the stimulation seen with the intact anti-Id.

Processing and Presentation of HBsAg and Anti-Id. APC are necessary for the uptake of complex antigen, degradation of the antigen in endosomal compartments into peptide fragments, and subsequent association of these peptides with MHC class II antigens on the surface of the APC. T cells specific for a given antigen then recognize this peptide-MHC class II complex and respond in in vitro proliferation assays by secreting IL-2 and proliferating. Proliferation can therefore be blocked by: (α) blocking the uptake of antigen into the APC (paraformaldehyde treatment of APC); (b) allowing uptake of the antigen into the APC but blocking degradation of the antigen into appropriate peptide fragments (chloroquine treatment of APC); or (c) blocking the association of the MHC class II antigen-peptide fragment complex to primed T cells with antibodies directed towards MHC class II antigens (anti-I-A or anti-I-E antibody treatment of APC).

Figure 2:
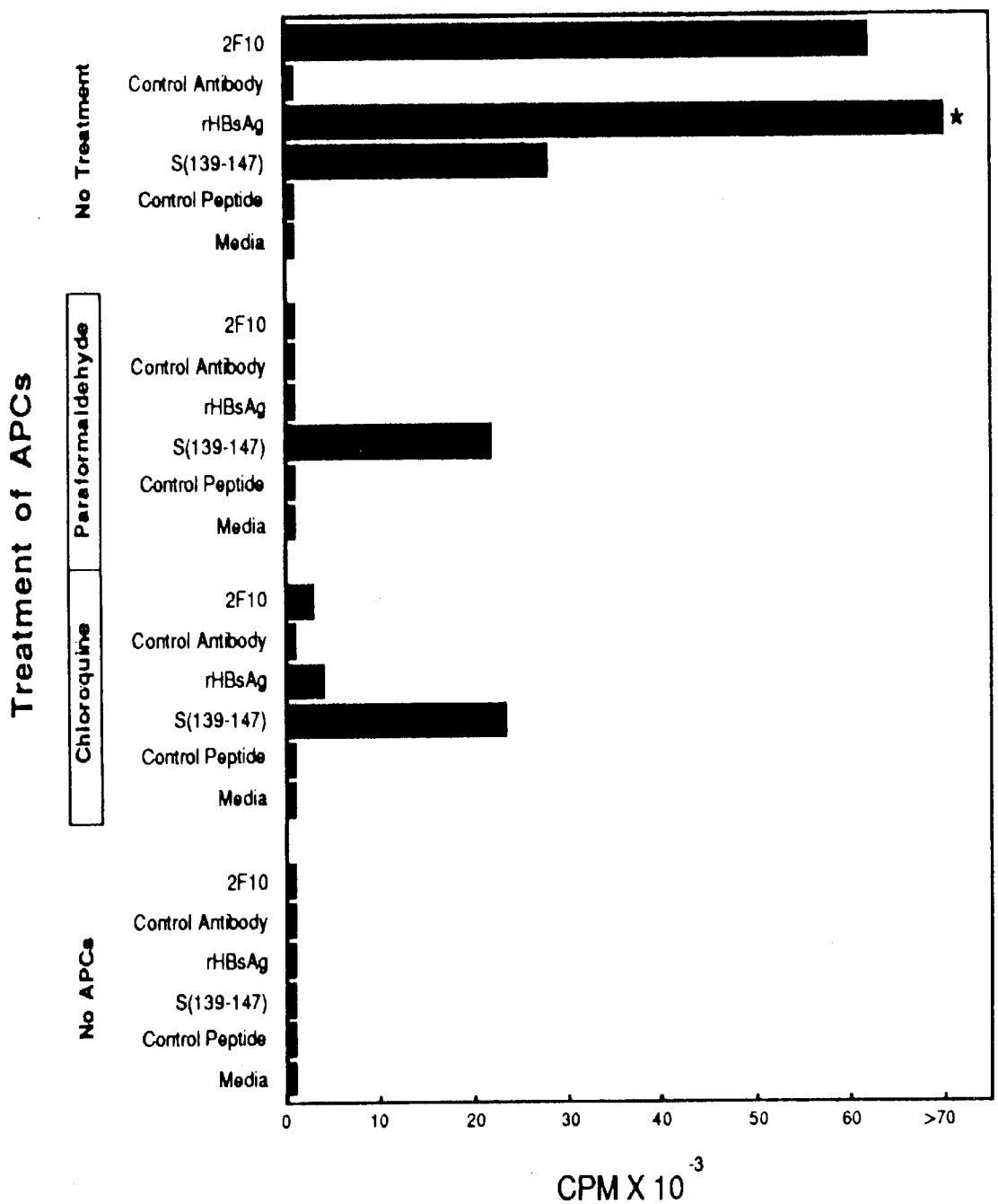
FIG. 2 shows a graph of in vitro proliferation assays wherein T cells were obtained from BALB/c mice that were injected with rHBsAg and set up in in vitro proliferation assays with the various stimuli shown on the y axis. Antigen presenting cells (APC) were treated with either chloroquine or paraformaldehyde. As can be seen, both of these protocols abrogate the in vitro proliferative responses to all stimuli except S(139–147) peptide. Results are expressed as the average cpm of [$^3$H]TdR incorporation of one experiment. In the absence of APC no response was observed.

It is known that HBsAg is a T-dependent antigen (Roberts-; I. M., et al., Nature (Lond.) 254:606 (1975)) and that the in vitro T cell proliferative responses to HBsAg are dependent upon APC. We therefore set out to determine if processing of the anti-Id was necessary before its presentation and recognition by primed T cells. Treatment of the APC with wither chloroquine or paraformaldehyde completely abrogated the in vitro T cell proliferative responses that were induced by priming in vivo with either HBsAg or anti-Id (FIG. 2). The response induced by the synthetic nine-amino acid peptide S(139–147), however, was not affected by this treatment and served as a positive control. Although results are only shown for T cells obtained from BALB/c mice injected with rHBsAg, similar results were obtained using anti-Id-primed BALB/c T cells.

Data in Table 5 are from experiments where BALB/c APC (H-2$^d$) were treated with either mAbs MK-D6 (anti-I-A$^d$) or 34-1-4S (anti-I-E$^d$). The results clearly show that the restriction for both anti-Id and HBsAg is imposed by the I-A$^d$ locus, as complete abrogation of the response is seen in cultures where the APC were treated with the anti-I-A$^d$-specific antibody. APC treated with anti-I-E$^d$ antibodies were able to present HBsAg/anti-Id similar to untreated cultures. Data from other laboratories have shown that both I-A$^d$- and I-E$^d$-encoded Ia molecules can present HBsAg in BALB/c mice (Milich, E. R., et al., J. Immunol. 134:4194 (1985)). The presence of APC was critical in our in vitro proliferation assay as no stimulation whatsoever was observed using rHBsAg/anti-Id-primed T cells stimulated by either antigen or anti-Id in the absence of APC (FIG. 2).

The surface envelope of HBV contains three related proteins designated S, M (S+preS2), and L (M+pre S1). All of these proteins share the 226-amino acid sequence of the S protein, which is the major protein of HBsAg. In a well documented series of experiments, it has been determined that the murine B and T cell responses to HBsAg are H-2 haplotype restricted and under the control of complex MHC class II region genes (Milich, D. R. et al., Immunol. Rev. 99:71 (1987)). It was therefore of great interest to us to determine if this pattern of restriction also applied to the responses generated by an anti-Id that mimics the group-specific a determinant on HBsAg. The studies presented here show that the B and T cell responses induced by our anti-Id 2F10 are apparently not restricted by the MHC haplotypes that we have tested, in that all mice immunized with 2F10 anti-Id, including the HBsAg nonresponder B10.M strain (H-2$^f$), made anti-HBs responses. These responses were specific for the a determinant, and the anti-HBs antibodies carried the Id to which the immunizing anti-Id had been raised (data not shown). Thus, 2F10 anti-Id was successful in circumventing S region nonresponsiveness in B10.M mice. The magnitude of the anti-HBs response induced by our anti-Id varied, with SWR and BALB/c eliciting a higher anti-HBs titer than B10.M and *M. spretus*. It should be noted that in our experiments the anti-Id was not coupled to any carrier protein for the induction of anti-HBs antibodies. Therefore, our anti-Id must contain both B and T cells epitopes to achieve this response. Milich et al. (J. Immunol. 137:315 (1986)) were also able to circumvent S region nonresponsiveness in B10.M mice by activation of the Th cell response to the pre S1 antigen, which could provide help not only to pre S1 specific but also to S-specific B cells with subsequent production of antibodies to the S region. This response, however, was not directed to the α determinant epitope.

Besides being able to induce an anti-HBs response, 2F10 anti-Id was also capable of priming in vivo T cells from SWR/J, BALB/c, and *M. spretus* that could subsequently proliferate in vitro to both anti-Id and HBsAg. The synthetic peptide S(139–147), which represents a partial α determinant epitope, could also stimulate anti-Id-primed T cells in vitro, further demonstrating the fidelity with which our anti-Id mimics the α determinant. It has been shown by others that anti-Id antibodies can influence specific T cell reactivity (Eichmann, K. et al., Crit. Rev. Immunol. 7:193 (1987); Sharpe, A. H., et al., J. Exp. Med. 160:1195 (1984); Rees, A. D. M., et al., Immunology, 60:389 (1987); and Rees, A. D. M., et al., Eur. J. Immunol. 17:197 (1987)). Thus, in the reovirus system, Sharpe et al., (J. Exp. Med. 160:1195 (1984)) have demonstrated that an internal image anti-Id that was raised against an antireovirus type 3 mAb could trigger T cell immunity (delayed type hypersensitivity and CTL responses) to reovirus type 3 in naive mice.

From the experiments described herein, it appears that the anti-Id is activating T cells through the same mechanisms used by nominal antigen. That is, stimulation of HBsAg/anti-Id-primed T cells by either HBsAg or anti-Id is accessory cell dependent and needs to be processed and presented to the T cells by APC in the context of class II MHC molecules. The in vitro proliferation that is observed using monovalent Fab fragments or isolated H chains rules out the possibility that our anti-Id is causing proliferation of these primed cells by crosslinking receptors on the T cells, as has been described with the anti-CD3 antibody (Landegren, U. et al., Eur. J. Immunol. 14:325 (1984.)). This is consistent with other reports of anti-Id activating antigen-primed T cells (Rees, A. D. M. et al., Immunology, 60:389 (1987) and Rees, A. D. M., et al., Eur. J. Immunol. 17:197 (1987)). Rees et al., Immunology, 60:389 (1987) have shown that a rabbit anti-ID that mimics a 38-kD protein purified from *Mycobacterium tuberculosis* could stimulate human PBL obtained from either *M. tuberculosis* patients or BCG-vaccinated individuals. It was determined that the proliferation elicited by the anti-Id was MHC restricted and dependent on interaction with APC (Rees, A. D. M. et al., Eur. J. Immunol. 17:197 (1987)).

It is interesting to note that the separation of intact anti-Id 2F10 into separate H and L chains revealed that the T cell epitope was located on the H chain since T cell proliferation to isolated H chains but not L chains was found to be comparable to that elicited by intact anti-Id. It is possible that the T cell stimulatory epitope on the H chain of the anti-Id also represents the B cell epitope. The above observations of 2F10 anti-Id mimicking HBsAg-specific B and T cell responses correlate well with recent data from our laboratory. Reducing SDS-PAGE followed by Western blot analysis revealed that the expression of the internal image epitope on anti-Id 2F10 was mainly localized to the H chain of the anti-Id. mRNA sequencing and molecular modeling experiments revealed an area of homology between the H chain and protective a determinant epitopes of HBsAg. A synthetic peptide that represents this region of homology can duplicate the B and T cell stimulatory responses of the intact anti-Id and the antigen that is mimicked, HBsAg (Price, M. W., et al., Proc. Natl. Acad. Sci. USA. 89:11900 (1992)). Additional support for T cell stimulatory epitopes also representing B cell epitopes comes from the influenza hemagglutinin system. It was observed that all of the hemagglutinin (HA1) synthetic peptides recognized by CD4+ T cell clones (specific for the HA of X31 virus [H3N2 subtype]) corresponded to residues that were contained within the primary sequence of HA1 B cell epitopes identified as a result of their recognition by neutralizing antibody (Graham, C. M. et al., Eur. J. Immunol. 19:523 (1989)).

Somewhat surprisingly, although 2F10 anti-Id generated an anti-HBs response in B10.M mice, it could not prime T cells that can be stimulated in vitro with HBsAg. This inertness of HBsAg in B10.M may be explained by the fact that: (α) B10.M mice may have a limited T cell repertoire that is lacking recognition structures with reasonable affinity for HBsAg/MHC combination (T cell hole); or (b) APC of B10.M mice may not process or present HBsAg in such a way that it can be recognized by anti-Id-primed T cells. These issues are being further explored. Preliminary data from this laboratory indicate that the reason anti-Id-primed B10.M T cells are unable to respond in vitro to HBsAg may be due to low affinity binding of the α determinant peptide to MHC class II molecules on B10.M APC (Rajadhyaksha, M. et al., J. Cell. Bio. Chem. 16D (Suppl.):69 (1992)). An alternative view for the inability of HBsAg to stimulate in vitro 2F10 anti-Id-primed B10.M T cells may be found in the work done in the GL antigen system (DeKruyff, R. H., et al., Eur. J. Immunol. 17:1115 (1987)). The synthetic random copolymer L-glutamic acid L-lysine (GL) is reported to be weakly or nonimmunogenic in all inbred strains of mice. Upon immunizing mice with the antigen poly(L-Glu L-Lys L-Tyr) (GLT), no in vitro response was observed when these primed T cells were stimulated with the antigen GL. However, after cloning these GLT-primed T cells, GL-reactive cells could be isolated at a high frequency. The same may be true with anti-Id-primed B10.M T cells.

Figure 3D:
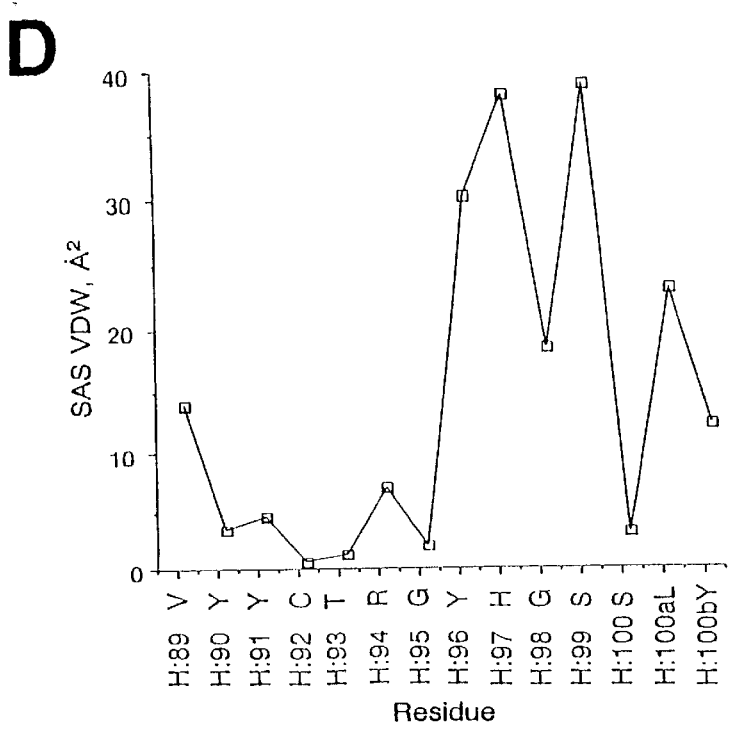

Determination of Epitopes on Anti-id 2F10 Responsible for Mimicking the a Determinant of HBsAg. Immunoglobulins carry antigenic determinants (ids), and id expression may or may not depend upon the combination of the H and L chains of the antibody. Reducing SDS/PAGE, followed by immunoblot analysis revealed that expression of the internal-image epitope on anti-id 2F10 did not depend upon the combination of H and L chains. The H chain of anti-id 2F10 was strongly detected with the $^{125}$I-labeled id (H3F5), whereas the L chain was only marginally detectable (FIG. 3A). Our earlier studies had established that T cells obtained from mice primed in vivo with the intact anti-id, responded vigorously in vitro to purified H chain but only minimally to purified L chain of anti-id 2F10 (Pride, M. W., et al., J. Exp. Med., Vol 177, pp 127–134, (1993).

To further delineate this anti-id epitope, we sequenced the H- and L-chain variable regions ($V_H$ and $V_L$, respectively) of mAb 2F10 by using standard mRNA sequencing techniques (Geliebter, J. Focus 9, 5–8 (1987)) and deduced the amino acid sequence. The primary amino acid sequences predicted for the $V_H$ and $V_L$ segments of mAb 2F10 are closely associated with the $V_H$ of the J558 family and the κ chain of the variable region of MOPC-149. We then compared amino acid sequences of the anti-id H and L chains with the known sequence of HBsAg by using the GAP algorithm (Needleman, S. B., et al., J. Mol. Biol. 48, 443–453 (1970)). We first compared amino acid sequences of the anti-id antibody with a 13-amino acid sequence on HBsAg [residues S-(135–146)], a region that represents a partial analogue of the group-specific aa determinant (Bhatnager, P. K., et al. Proc. Natl. Acad. Sci. USA 79, 4400–4404 (1982)). This alignment showed a 58% similarity and 25% identity between HBsAg-(135–146) and a region encompassing the third complementarity-determining region, (CDR3) and part of the adjacent framework (FR3) of the 2F10 H chain (H:88–99: FIG. 1β). We also searched for alignment between amino acids in the FR3 and CDR3 regions on the anti-id H chain and the complete HBsAg sequence (226 residues). We obtained values of 60% similarity and 30%s identity for a sequence of 11 residues (124–134) of HBsAg that were adjacent to the 13 residues used in the previous alignment. This region of HBsAg is also believed to contain a partial group a determinant epitope of HBsAg (Ionescu-Matiu, I., et al., J. Immunol. 130, 1947–1952 (1983)). FIG. 3B shows the alignment obtained. No sequence homology was observed between the V region of the 2F10 L chain and HBsAg.

Genetic variants of HBV (arising from immunological pressure) have been defined, which correspond to amino acid substitutions within the protective a determinant region of HBsAg [S-(139–147)] (McMahon, G., et al., Hepatology 115, 757–776 (1992) and Carman, W. F., et al., Lancet 336, 325–329 (1990)). These reports demonstrated an identical amino acid substitution of Gly-145→Arg in the S protein of HBV. Recent studies using synthetic peptides corresponding to residues S-(139–147) of HBsAg, with a Gly-145→Arg substitution demonstrated a decrease in antigenicity and abrogation of in vitro proliferative responses of both human and mouse T cells primed in vivo to HBsAg (Neurath, A. R. et al, Peptide Res. 3, 116–122 (1990)). It is important to note that this glycine residue is conserved within the sequence of the anti-id 2F10 H chain that we have identified as homologous to the a determinant region of HBsAg. Some other important residues to consider correspond to positions that distinguish serological subtypes of HBV from each other and additionally some positions for which information is available on amino acid replacement and its effect on immunological reactivity of HBsAg. Lysine occupies position 141 in the HBsAg sequence, whereas arginine occupies that position in the anti-id sequence. However, we have previously shown, by deliberate amino acid replacement, that a Lys→Arg substitution at this position does not alter the ability of the peptide to elicit T-cell proliferation of human cells in vitro (Neurath, A. R. et al, Peptide Res. 3, 116–122 (1990)). On the other hand, at position 142 there is a proline in the HBsAg sequence and a lycine in the anti-id 2F10 sequence. The presence of a glycine or an isoleucine at this position has been reported to decrease the antigenicity of HBsAg (Ashton-Rickardt, P. G. & Murray, K., J. Med. Virol. 29, 196–203 (1989)) At position 143 there is either a serine or a threonine, depending on the HBV subtype; we observe a tyrosine at this position in the 2F10 peptide sequence. The effect of such a replacement at this position on the immunogenicity of HBsAg is presently unknown.

Threonine occupies position 126 in almost all HBV subtypes (except adr, which has an isoleucine); in the anti-id sequence there is an arginine at this position. However, from replacement set analysis we know that an arginine replacement does not alter in vitro proliferation of human T cells obtained from HBsAg-vaccinated donors (Pride, M. W., et al., Peptide Res. 5, 217–226, (1992)). At position 131 there is a threonine instead of an asparagine, corresponding to subtypes ayw and adw, respectively; serine at this position in the anti-id sequence would relate the residue more closely to threonine than to asparagine. Additionally, we know (Pride, M. W., et al., Peptide Res. 5, 217–226, (1992)) that deliberate replacement of serine at this position is tolerated at the level of human T-cell proliferation. All subtypes except adw have methionine at position 133, and in the anti-id we report that presence of leucine. However, experiments with replacement set analysis have already established that Met/Lys→Leu is immunologically tolerated (Pride, M. W., et al., Peptide Res. 5, 217–226, (1992)). Finally, subtype ayw has a Tyr-134, also present in the anti-id sequence. The presence of tyrosine rather than phenylalanine at position 134 was also reported by Charnay et al. (Nucleic Acids Res. 7, 335–346 (1979)) and Pasek et al. (Nature (London) 282, 575–579 (1979)).

To visualize this epitope, computer-assisted molecular modeling of the H and L chains CDRs of mAb 2F10 was completed, using canonical immunoglobulin structure libraries, energy-minimization techniques, and molecular dynamics simulations (Chothia, C. et al, J. Mol. Biol. 196, 901–917 (1987); Chothia, C. et al., Nature (London) 342, 877–883 (1989); Kussie, P. H. et al., J. Immunol. 146, 4248–4257 (1991); and Brooks, B. R. et al., J. Comput. Chem. 4, 187–217 (1983)). Visual and computational inspection (FIG. 3 C and D) of the completed mAb 2F10 Fv model revealed that H-chain amino acids in positions H:96–H:100b (FIG. 3D) had considerable surface solvent accessibility [determined by the algorithm ACCESS (Lee, B. et al., J. Mol. Biol. 55, 379–500 (1971)]. These data and the fact that secondary-structural analysis of this area revealed a β-turn, support the prediction that this region is probably antigenic (McMillan, S., et al., Cell 45, 859–863 (1983) and Wilson, I., et al., Cell 37, 767–778 (1984)). Additionally, such CDR loop motifs have been shown to be highly antigenic as idiotypic determinants and have been identified as the determinants responsible for anti-id molecular mimicry in another system (Bruck C., et al., Proc. Natl. Acad. Sci. USA 83, 6578–6582 (1986)). Based on the sequence homology searches and examination of the computer-assisted molecular modeling, we elected to synthesize a 15-mer peptide (AVYYCTRGYHGSSLY) , referred to as 15-mer 2F10 peptide. This peptide was tested to determine whether it could duplicate the in vitro and in vivo properties displayed by the intact anti-id 2F10 mAb.

Figure 4A:
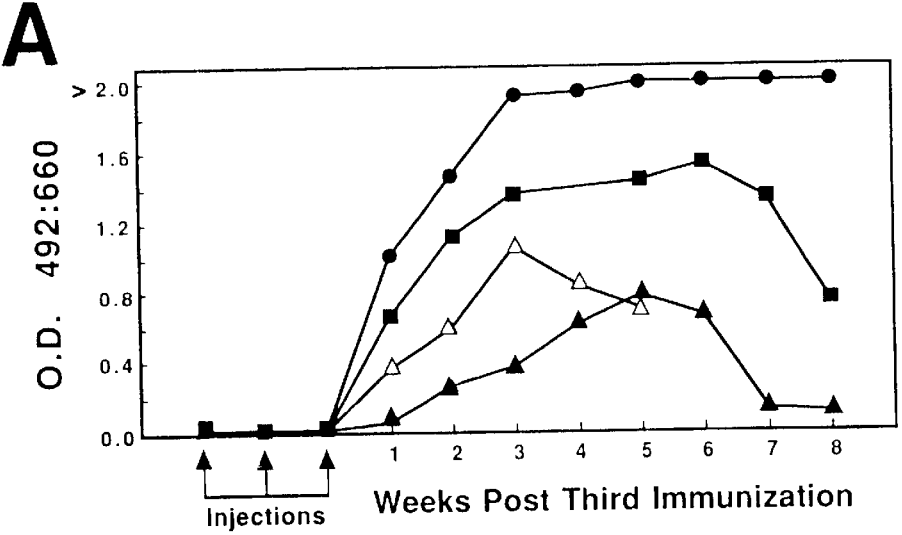
FIGS. 4A–4B show graphs illustrating that 2F10 15-mer peptide can elicit anti-HBsAg antibodies in vivo and can prime T-cells for an in vitro HBsAg- specific T-cell proliferative response in BALB/c mice.

Anti-id 15-mer Peptide Can Induce Antibodies to the Antigen That the Peptide Mimics. FIG. 4A shows that 15-mer 2F10 peptide covalently coupled to KLH could successfully elicit anti-HBsAg antibodies when administered to BALB/c mice, although the response was less than that seen after injection of rHBsAg or intact 2F10. Anti-HBsAg antibodies were also elicited when mice were immunized with the peptide alone (not conjugated to a protein carrier), providing the initial evidence that this 15-mer contained not only a B- but also a T-cell epitope [the antibody response to HBsAg is strictly T-cell dependent].

Figure 4B:
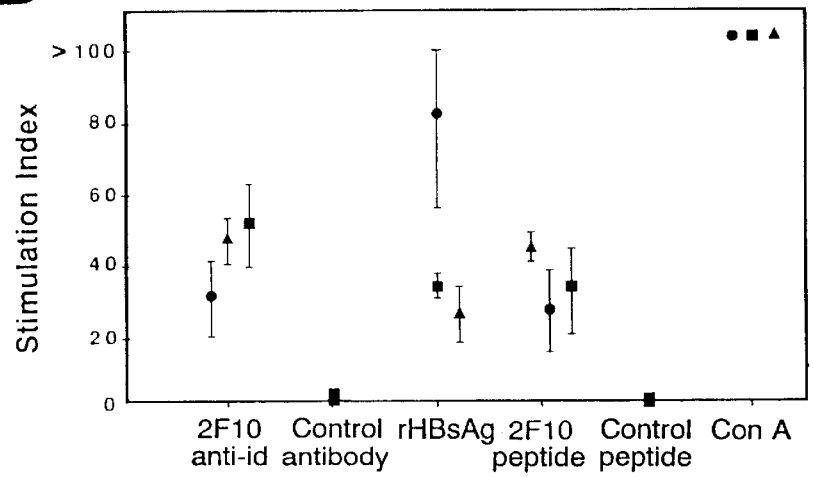

Mouse T-Cell Stimulation. To provide further evidence that the 15-mer 2F10 peptide contained a T-cell stimulatory epitope, BALB/c mice were primed in vivo with the 15-mer 2F10 peptide, and the primed T cells were tested for their ability to proliferate in vitro to the appropriate stimuli. FIG. 4B shows that T cells obtained from mice primed in vivo with 15-mer 2F10 peptide can respond in vitro to 15-mer 2F10 peptide and intact 2F10. More importantly, proliferation also occurs after in vitro stimulation with HBsAg. This result has significance in considering the use of this anti-id peptide as an alternative vaccine. For comparison, mice were also immunized with rHBsAg or the intact anti-id. Primed T cells from each group could also be appropriately stimulated (FIG. 4B).

Figure 5:
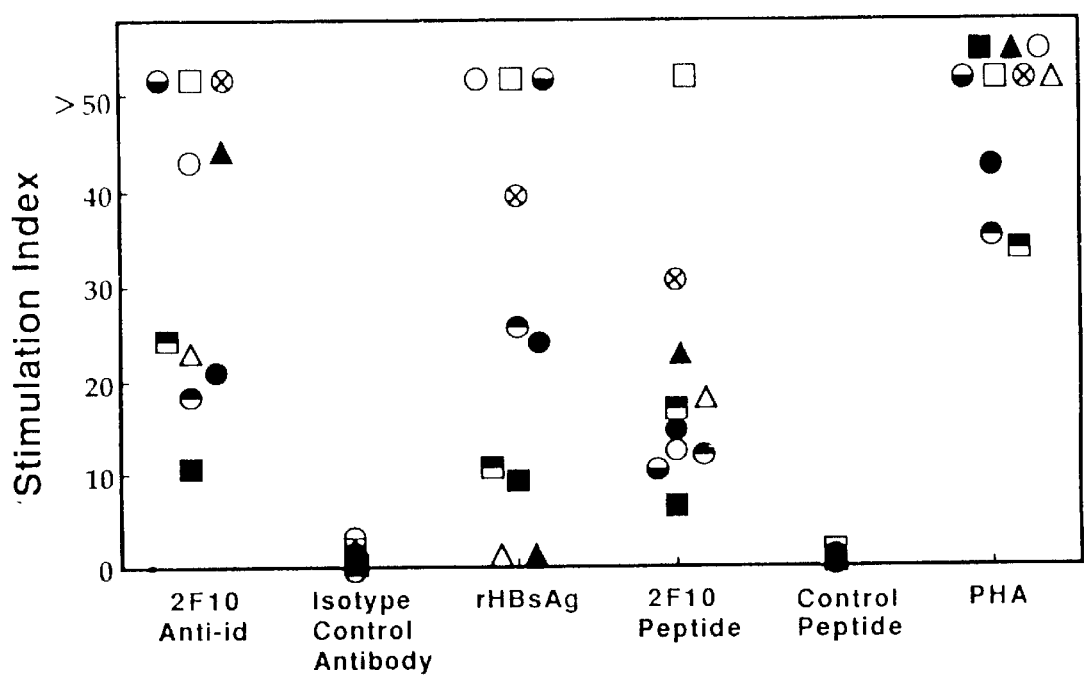
FIG. 5 shows that anti-Id peptide can stimulate human CD4+ cells in vitro that were primed in vivo as a result of vaccination with the licensed hepatitis B vaccine (RecombiVax, HB; ⊖, ⊗, ⊖, ○, ●); natural infection with the hepatitis B virus (■, □, ▬,), and hepatitis B carriers (Δ, ▲). In vitro stimuli are the same as for FIG. 2B, except phytohemagglutinin (PHA) was used instead of Con A. Each symbol represents one person.

Human T-Cell Stimulation. To demonstrate the efficacy of our anti-id 15-mer peptide in a more clinically relevant system, human CDR$^+$ T cells from individuals primed in vivo by vaccination or from HBV infection were cultured in in vitro proliferation assays with a panel of different stimuli. The results of FIG. 5 clearly establish that anti-id 2F10 15-mer peptide can stimulate in vitro human CD4$^+$ T cells primed in vivo by vaccination with the licensed hepatitis B vaccine (i.e., individuals serologically HBsAg$^-$, anti-HBsAg$^+$, anti-HBcAg$^-$). These findings agree with those of FIG. 2B with T cells from mice immunized with rHBsAg. Individuals primed in vivo to HBsAg from infection with HBV are distinguished serologically as HBsAg$^-$, anti-HBsAg$^+$, anti-HBcAg$^+$ (naturally infected and recovered individuals) or as HBsAg$^+$, anti-HBsAg$^-$, anti-HBcAg$^+$ (HBV carriers). In a manner analogous to that reported above for vaccinated individuals, CD4$^+$ T cells from naturally infected and immune individuals could also be stimulated in vitro by anti-id 15-mer peptide, intact anti-id antibody, and rHBsAg. Thus, 2F10 anti-id 15-mer peptide could stimulate CD4$^+$ T cells primed in vivo either as a result of vaccination or exposure to live virus.

Figure 3C:
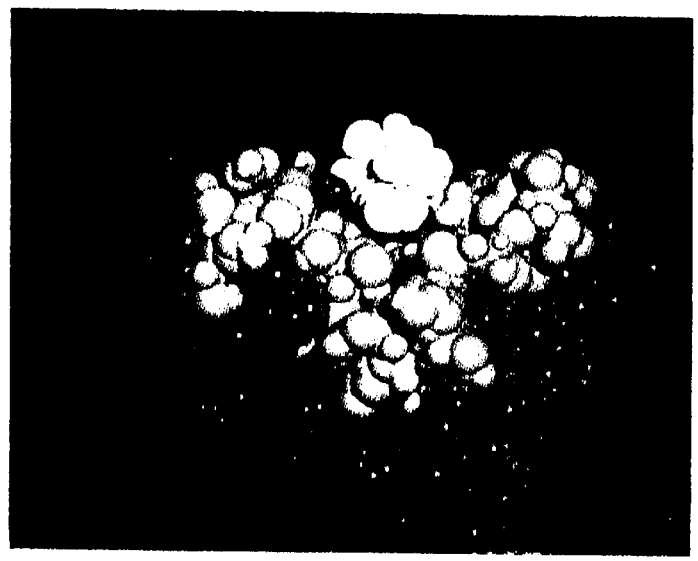

Before synthesis of the 15-mer 2F10 peptide, we had demonstrated that the intact anti-id antibody could stimulate CD4$^+$ T cells from 27 HBV carriers. When the anti-id 2F10 15-mer peptide became available, we had the opportunity to test its usefulness in two additional HBV carrier patients (FIG. 3). It is significant to note that 2F10 15-mer peptide and intact 2F10, which both mimic HBsAg, can stimulate CD4$^+$ T cells from HBV carriers, whereas the native antigen, HBsAg, cannot. It may be argued that this anti-id antibody is stimulating T cells nonspecifically by T-cell receptor crosslinking; however, the stimulation seen with the monovalent Fab fragment of the anti-id. (data not shown) and the anti-id 2F10 15-mer peptide refutes this possibility. No in vitro responses were elicited with peripheral blood mononuclear cells from nonimmune individuals (HBsAg$^-$, anti-HBsAg$^-$, anti-HBcAg$^-$), thus establishing specificity of the assay (data not shown).

Mimicry of external antigens by internal-image anti-id epitopes can occur by either analogous or cross-reactive homologous id mimicry. As in nature, where most mimicry is analogous, the same is true for anti-id mimicry, where elementary interactive components (electrostatic, H bonding, van der Waals, etc.) contribute to the formation of a three-dimensional region on the anti-id antibody responsible for mimicry of the external antigen. Thus, where anti-id epitopes mimic carbohydrate or lipid epitopes, mimicry is obviously established by a functional conformation rather than identity at the primary-amino acid-sequence level.

The whole anti-idiotypic 2F10 antibody was tested for human response as described above with respect to the anti-id peptide. The 2F10 antibody was tested against three groups. Group 1 were previously vaccinated with the licensed hepatitis B vaccine, group 2 were infected with hepatitis B and recovered and group 3 were infected with hepatitis B and became carriers. In all cases, a response was found using the whole 2F10 antibody in a manner parallel to the use of the peptide above described.

Although many investigators have reported the existence of anti-id antibodies and their relative usefulness as surrogate antigens, only limited reports testify to anti-id mimicry due to homologous cross-reactive id mimicry. Ollier et al. (EMBO J. 4, 3681–3688 (1985)) have shown that the diversity region of the H-chain segment of an internal-image anti-id mAb presents a Glu-Ala-Tyr (GAT)-like epitope. In the rabbit al allotype system, two anti-id mAbs were produced that show al-like internal image. mRNA sequencing of these anti-id proteins revealed amino acid homology on the $V_H$ (CDR2) with the nominal antigen, however, in reverse orientation. Synthetic peptides made from this al-like region could inhibit the binding of al immunoglobulin to anti-al antibody (VanCleave, V. H. et al., 167, 1841–1848 (1988)). No in vivo B- or T-cell responses to either of these anti-id peptides have yet been reported. Clearly, the best-studied system to date of cross-reactive homologous epitope mimicry is the work in the reovirus type 3 system (Bruck, C., et al., Proc. Natl. Acad. Sci. USA 83, 6578–6582 (1986); Williams, W. V., et al., Proc. Natl. Acad. Sci. USA 85, 6488–6492 (1988) and Williams, W. V. et al., J. Immunol. 142, 4392–4400 (1989)). By amino acid sequencing and computer-modeling procedures, homology between a portion of the hemagglutinin on the reovirus type 3 and the variable regions of an anti-id mAb has been shown (Bruck, C. et al., Proc. Natl. Acad. Sci. USA 83, 6578–6582 (1986)). Synthetic peptides from these regions of homology on the anti-id ($V_H$ and $V_L$) antibody show quite different biological effects (Williams, W. V. et al., J. Immunol. 142, 4392–4400 (1989)). The $V_L$ peptide defines a predominant B-cell epitope (which induces potent neutralizing antibodies) and an epitope that is important in delayed-type hypersensitivity responses to the reovirus type 3 hemagglutinin. However, the $V_H$ peptide defines a major helper T-cell epitope on the anti-id that is recognized by reovirus type 3-induced helper T cells.

We have not only identified the homology between the anti-id region and the a determinant of HBsAg but have also demonstrated that a synthetic peptide representing this area of homology can mimic native HBsAg by eliciting specific B- and T-cell responses in vivo and in vitro. One of the limitations of most synthetic peptides is that they fail to produce a secondary protective immune response due to a lack of an anamnestic recognition of helper T-cell epitopes. Sharing of ids between T and B cells of related antigen specificity would permit use of the same anti-id/anti-id-derived peptide to activate both T and B cells for an anamnestic recognition of similar epitopes on the infectious organism. We have demonstrated that the anti-id 2F10 can stimulate antigen-specific B and T cells and that a 15-amino acid synthetic peptide can duplicate these responses. This aspect may circumvent the problem of using nonhuman antibody preparations (mouse monoclonal anti-id) in human subjects. Additionally, the responses seen using anti-id/anti-id-derived peptide in stimulating HBV carrier CD4$^+$T cells are promising and may also have relevance in individuals who are nonresponders to the licensed HBV vaccine. The cellular mechanism for unresponsiveness to HBsAg at the T-cell level in HBV carriers has not been determined. Antigen-specific suppressor mechanisms and genetically determined nonrecognition have been implicated (Ferrari, C., et al., J. Hepatol. 7, 21–33 (1988)). The anti-id and anti-id peptide may overcome these limitations because they mimic only a limited portion of the HBsAg sequence, do not carry suppressor epitopes, and can probably be recognized by a wide range of human major histocompatibility complex haplotypes. These results strongly support the usefulness of the 2F10 15-mer peptide, not only for experimental animal models but also in a clinically relevant human system.

TABLE 1

Isotype Distribution of Anti-HBs Responses

| Mouse | Immunogen | IgG1 | IgG2a | IgG2b | IgG3 | IgM |
|---|---|---|---|---|---|---|
| BALB/c (H-$2^d$) | None* | 0.042 | 0.035 | 0.041 | 0.048 | 0.047 |
| | 2F10<sup>l</sup> | 1.289 | 0.069 | 0.020 | 0.075 | 0.097 |
| | 2F10<sup>f</sup> | 0.919 | 0.080 | 0.180 | 0.033 | 0.126 |
| | 2C3<sup>∥</sup> | 0.064 | 0.041 | 0.058 | 0.069 | 0.064 |
| | HBsAg<sup>f</sup> | 1.686 | 0.219 | 0.814 | 0.095 | 0.238 |
| B10.M (H-$2^f$) | None* | 0.027 | 0.004 | 0.045 | 0.008 | 0.032 |
| | 2F10<sup>¶</sup> | 0.245 | 0.026 | 0.892 | 0.089 | 0.096 |
| | 2C3** | 0.048 | 0.022 | 0.032 | 0.065 | 0.052 |
| | HBsAg<sup>∥</sup> | 0.040 | 0.039 | 0.028 | 0.035 | 0.027 |

Comparison of the isotype distribution of the anti-HBs response in BALB/c and B10.M mice immunized with anti-Id 2F10, isotype control antibody 2C3, or rHBsAg. Sera were collected 1 wk after the third injection (unless indicated otherwise) and tested at a 1:50 dilution. Results are expressed as OD at 405 nm.
*Pooled normal sera. Values are the average of four separate experiments.
<sup>l</sup>Values represent the average of six mice.
<sup>f</sup> Values represent the average of sera from one mouse bled 3, 4, and 5 wk after the third injection.
<sup>∥</sup> Values represent the average of two mice.
<sup>¶</sup> Values represent the average of sera from two mice bled 3, 4, and 5 wk after the third injection.
**Values represent the average of three mice.

TABLE 2

In Vitro Proliferation of BHsAg-primed T Cells

| Stimulus | Concentration μg/well | BALB/c (H-$2^d$) | SWR/J (H-$2^g$) | B10.M (H-$2^f$) |
|---|---|---|---|---|
| 2F10 | 20 | 43,842 | 54,172 | 908 |
| | 50 | 66,066 | 86,121 | 746 |
| 2F10 Fab | 20 | ND | 54,648 | ND |
| 2F10 H chain | 20 | 43,812 | 45,283 | ND |
| 2F10 L chain | 20 | 4,089 | ND | ND |
| 2C3 | 20 | 1,238 | 296 | 593 |
| | 50 | 1,248 | 305 | 773 |
| rHBsAg | 0.1 | 49,628 | 72,044 | 717 |
| | 0.5 | 41,533 | 109,513 | 762 |
| Peptide | 0.05 | 21,799 | 45,190 | 762 |
| S(139–147) | 0.1 | 27,107 | 17,307 | 559 |
| Control | 0.05 | 408 | 113 | 602 |
| Peptide | 0.1 | 340 | 469 | 816 |
| Media | | 761 | 276 | 823 |

HBsAg and 2F10 anti-Id can stimulate in vitro T cells from mice of different H-2 haplotypes (except B10.M) that were primed in vivo with HBsAg. Proliferation was assessed as described in Materials and Methods. Results are expressed as the average cpm of PHITdR incorporation of either four (BALB/c), two (B10.M), or one (SWR/J) separate experiment.

TABLE 3

In Vitro Proliferation of Anti-Id-Primed T Cells

| Stimulus | Concentration μg/well | BALB/c (H-$2^f$) | SWR/J (H-$2^f$) | B10.M (H-$2^f$) | M. spretus |
|---|---|---|---|---|---|
| 2F10 | 20 | 160,495 | 46,669 | 35,695 | 49,068 |
| | 50 | 161,501 | 54,413 | 48,494 | 75,005 |
| 2F10 Fab | 20 | ND | 46,340 | ND | 54,660 |
| 2F10 H chain | 20 | ND | 34,233 | ND | 44,746 |
| 2C3 | 20 | 2,167 | 739 | 441 | 357 |
| | 50 | 2,483 | 543 | 358 | 645 |
| rHBsAg | 0.1 | 43,682 | 42,995 | 791 | 46,406 |
| | 0.5 | 52,557 | 53,953 | 771 | 61,225 |
| Peptide | 0.05 | 21,668 | 44,840 | 408 | 36,548 |
| S(139–147) | 0.1 | 26,296 | 32,984 | 368 | 22,825 |
| Control | 0.05 | 1,707 | 973 | 560 | 539 |
| Peptide | 0.1 | 1,836 | 699 | 527 | 601 |
| Media | | 2,255 | 1,039 | 420 | 554 |

HBsAg and 2F10 anti-Id can stimulate in vitro T cells from mice of different H-2 haplotypes that were primed in vivo with 2F10 anti-Id. In every strain tested 2F10 anti-Id can induce an anti-HBs response, however, it cannot prime T cells in the B10.M(H-$2^f$) strain that can be recalled in vitro by HBsAg. Proliferation was assessed as described in Materials and Methods. Results are expressed as the average cpm of [$^3$H]TdR incorporation of either two (B10.M) or one (BALB/c, SWR/J, M. spretus) separate experiments.

TABLE 4

In Vitro Proliferation of Isotype Control Antibody-primed T Cells

| Stimulus | Concentration μg/well | BALB/c (H-$2^d$) |
|---|---|---|
| 2F10 | 20 | 548 |
| | 50 | 987 |
| 2C3 | 20 | 11,066 |
| | 50 | 15,566 |
| rHBsAg | 0.1 | 40 |
| | 0.5 | 547 |
| Peptide | 0.05 | 937 |
| S(139–147) | 0.1 | 1,073 |
| Control | 0.05 | 1,113 |
| Peptide | 0.1 | 1,167 |
| Media | | 757 |

Specificity control for anti-Id 2F10. BALB/c mice were primed in vivo with isotype-matched control mAb 2C3 (IgG1,k). Primed T cells from these mice cannot be stimulated in vitro by either anti-Id or HBsAg. Proliferation was assessed as described in Materials and Methods. Results are expressed as the average cpm of PHITdR incorporation of two separate experiments.

TABLE 5

The Effect on T Cell Proliferation after Treatment of APC with Anti-Ig Reagents

| | | APC treatment | | | | | |
|---|---|---|---|---|---|---|---|
| | Concentration | rHBsAg-primed T cells | | | Anti-Id-primed T cells | | |
| Stimulus | μg/well | No treatment | Anti-I-A$^d$ | Anti-I-E$^d$ | No treatment | Anti-I-A$^d$ | Anti-I-E$^d$ |
| 2F10 | 50 | 59,132 | 3,090 | 43,867 | 65,920 | 1,537 | 56,101 |
| 2C3 | 50 | 716 | 412 | 390 | 655 | 294 | 562 |
| rHBsAg | 0.1 | 82,405 | 2,505 | 81,327 | 54,228 | 396 | 35,678 |
| Peptide S(139–147) | 0.1 | 42,571 | 3,400 | 48,373 | 43,873 | 346 | 21,544 |
| Control Peptide | 0.1 | ND | ND | ND | 563 | 256 | 421 |
| Media | | 408 | 346 | 627 | 189 | 343 | 461 |

In vitro proliferation of T cells primed with either rHBsAg or 2F10 anti-Id are restricted at the I-A$^d$ locus in BALB/c mice. This is seen by the significant decrease of proliferation in cultures treated with MK-D6 (anti-I-A$^d$ antibody) versus those treated with 34-I-4S (anti-I-E$^d$ antibody) or no treatment. Proliferation was assessed as described in Materials and Methods. Results are expressed as the average cpm of [$^3$H]TdR incorporation of two separate experiments.

---

What is claimed is:

1. A method for detecting an immune response of an individual to Hepatitis B which comprises contacting serum from the individual with the 15 amino acid sequence Ala Val Tyr Tyr Cys Thr Arg Gly Tyr His Gly Ser Ser Leu Tyr (Sequence ID #1) and detecting a response to said sequence.

2. A method for detecting an immune response of an individual to Hepatitis B which comprises contacting serum from the individual with the 8 amino acid sequence Gly Tyr His Gly Ser Ser Leu Tyr (Sequence ID #2) and detecting a response to said sequence.

* * * * *

UNITED STATES PATENT AND TRADEMARK OFFICE
CERTIFICATE OF CORRECTION

| | | |
|---|---|---|
| PATENT NO. | : 5,856,087 | Page 1 of 1 |
| APPLICATION NO. | : 08/948762 | |
| DATED | : January 5, 1999 | |
| INVENTOR(S) | : Yasmin Thanvala et al. | |

It is certified that error appears in the above-identified patent and that said Letters Patent is hereby corrected as shown below:

In Column 1, line 8, delete,

"This work is sponsored by the National Institute of Health Grant Nos. AI-24328 and AI-27976. The U.S. Government may have certain rights in this invention."
and insert,
--STATEMENT REGARDING FEDERALLY SPONSORED RESEARCH
    This invention was made with government support under AI024328 and AI027976 awarded by the National Institutes of Health. The government has certain rights in the invention.--

Signed and Sealed this
Nineteenth Day of June, 2012

David J. Kappos
*Director of the United States Patent and Trademark Office*

SEQUENCE LISTING ( 1 ) GENERAL INFORMATION:

( i i i ) NUMBER OF SEQUENCES: 12

( 2 ) INFORMATION FOR SEQ ID NO: 1:

( i ) SEQUENCE CHARACTERISTICS:
        ( A ) LENGTH: 15
        ( B ) TYPE: AMINO ACID
        ( C ) STRANDEDNESS: UNKNOWN
        ( D ) TOPOLOGY: UNKNOWN ( i i ) MOLECULE TYPE: PEPTIDE ( i i i ) HYPOTHETICAL: NO ( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:

(G) DATE:
                (H) DOCUMENT NUMBER:
                (I) FILING DATE:
                (J) PUBLICATION DATE:
                (K) RELEVANT RESIDUES IN SEQ ID NO:

(ix) SEQUENCE DESCRIPTION: SEQ ID NO: 1:

```
Ala  Val  Tyr  Tyr  Cys  Thr  Arg  Gly  Tyr  His  Gly  Ser  Ser  Leu  Tyr
 1              5                        10                       15
```

(2) INFORMATION FOR SEQ ID NO: 2:

(i) SEQUENCE CHARACTERISTICS:
                (A) LENGTH: 8
                (B) TYPE: AMINO ACID
                (C) STRANDEDNESS: UNKNOWN
                (D) TOPOLOGY: UNKNOWN (ii) MOLECULE TYPE: PEPTIDE (iii) HYPOTHETICAL: NO (iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(ix) SEQUENCE DESCRIPTION: SEQ ID NO: 2:

```
Gly  Tyr  His  Gly  Ser  Ser  Leu  Tyr
 1              5
```

(2) INFORMATION FOR SEQ ID NO: 3:

(i) SEQUENCE CHARACTERISTICS:
                (A) LENGTH: 3
                (B) TYPE: AMINO ACID
                (C) STRANDEDNESS: UNKNOWN
                (D) TOPOLOGY: UNKNOWN (ii) MOLECULE TYPE: PEPTIDE (iii) HYPOTHETICAL: NO (iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

(vii) IMMEDIATE SOURCE:
            (A) LIBRARY:
            (B) CLONE:

(viii) POSITION IN GENOME:
            (A) CHROMOSOME/SEGMENT:
            (B) MAP POSITION:
            (C) UNITS:

(ix) FEATURE:
            (A) NAME/KEY:
            (B) LOCATION:
            (C) IDENTIFICATION METHOD:
            (D) OTHER INFORMATION:

(x) PUBLICATION INFORMATION:
            (A) AUTHORS:
            (B) TITLE:
            (C) JOURNAL:
            (D) VOLUME:
            (E) ISSUE:
            (F) PAGES:
            (G) DATE:
            (H) DOCUMENT NUMBER:
            (I) FILING DATE:
            (J) PUBLICATION DATE:
            (K) RELEVANT RESIDUES IN SEQ ID NO:

(ix) SEQUENCE DESCRIPTION: SEQ ID NO: 3:

Ser Leu Tyr
 1

(2) INFORMATION FOR SEQ ID NO: 4:

(i) SEQUENCE CHARACTERISTICS:
            (A) LENGTH: 4
            (B) TYPE: AMINO ACID
            (C) STRANDEDNESS: UNKNOWN
            (D) TOPOLOGY: UNKNOWN (ii) MOLECULE TYPE: PEPTIDE (iii) HYPOTHETICAL: NO (iv) ANTI-SENSE:

(v) FRAGMENT TYPE:

(vi) ORIGINAL SOURCE:
            (A) ORGANISM:
            (B) STRAIN:
            (C) INDIVIDUAL ISOLATE:
            (D) DEVELOPMENTAL STAGE:
            (E) HAPLOTYPE:
            (F) TISSUE TYPE:
            (G) CELL TYPE:
            (H) CELL LINE:
            (I) ORGANELLE:

( v i i ) IMMEDIATE SOURCE:
      ( A ) LIBRARY:
      ( B ) CLONE:

( v i i i ) POSITION IN GENOME:
      ( A ) CHROMOSOME/SEGMENT:
      ( B ) MAP POSITION:
      ( C ) UNITS:

( i x ) FEATURE:
      ( A ) NAME/KEY:
      ( B ) LOCATION:
      ( C ) IDENTIFICATION METHOD:
      ( D ) OTHER INFORMATION:

( x ) PUBLICATION INFORMATION:
      ( A ) AUTHORS:
      ( B ) TITLE:
      ( C ) JOURNAL:
      ( D ) VOLUME:
      ( E ) ISSUE:
      ( F ) PAGES:
      ( G ) DATE:
      ( H ) DOCUMENT NUMBER:
      ( I ) FILING DATE:
      ( J ) PUBLICATION DATE:
      ( K ) RELEVANT RESIDUES IN SEQ ID NO:

( i x ) SEQUENCE DESCRIPTION: SEQ ID NO: 4:

Ser  Ser  Leu  Tyr
 1

( 2 ) INFORMATION FOR SEQ ID NO: 5:

( i ) SEQUENCE CHARACTERISTICS:
      ( A ) LENGTH: 9
      ( B ) TYPE: AMINO ACID
      ( C ) STRANDEDNESS: UNKNOWN
      ( D ) TOPOLOGY: UNKNOWN ( i i ) MOLECULE TYPE: PEPTIDE ( i i i ) HYPOTHETICAL: NO ( i v ) ANTI-SENSE:

( v ) FRAGMENT TYPE:

( v i ) ORIGINAL SOURCE:
      ( A ) ORGANISM:
      ( B ) STRAIN:
      ( C ) INDIVIDUAL ISOLATE:
      ( D ) DEVELOPMENTAL STAGE:
      ( E ) HAPLOTYPE:
      ( F ) TISSUE TYPE:
      ( G ) CELL TYPE:
      ( H ) CELL LINE:
      ( I ) ORGANELLE:

( v i i ) IMMEDIATE SOURCE:
      ( A ) LIBRARY:
      ( B ) CLONE:

( v i i i ) POSITION IN GENOME:
      ( A ) CHROMOSOME/SEGMENT:
      ( B ) MAP POSITION:
      ( C ) UNITS:

( i x ) FEATURE:
      ( A ) NAME/KEY:
      ( B ) LOCATION:
      ( C ) IDENTIFICATION METHOD:
      ( D ) OTHER INFORMATION:

( x ) PUBLICATION INFORMATION:
      ( A ) AUTHORS:
      ( B ) TITLE:

(C) JOURNAL:
(D) VOLUME:
(E) ISSUE:
(F) PAGES:
(G) DATE:
(H) DOCUMENT NUMBER:
(I) FILING DATE:
(J) PUBLICATION DATE:
(K) RELEVANT RESIDUES IN SEQ ID NO:

(ix) SEQUENCE DESCRIPTION: SEQ ID NO: 5:

Cys Thr Lys Pro Thr Asp Gly Asn Cys
 1                   5

(2) INFORMATION FOR SEQ ID NO: 6:

(i) SEQUENCE CHARACTERISTICS:
    (A) LENGTH: 9
    (B) TYPE: AMINO ACID
    (C) STRANDEDNESS: UNKNOWN
    (D) TOPOLOGY: UNKNOWN (ii) MOLECULE TYPE: PEPTIDE (iii) HYPOTHETICAL: NO (iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY:
    (B) LOCATION:
    (C) IDENTIFICATION METHOD:
    (D) OTHER INFORMATION:

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(ix) SEQUENCE DESCRIPTION: SEQ ID NO: 6:

Cys Thr Lys Pro Ser Asp Arg Asn Cys
 1                   5

(2) INFORMATION FOR SEQ ID NO: 7:

(i) SEQUENCE CHARACTERISTICS:

(A) LENGTH: 15
                (B) TYPE: AMINO ACID
                (C) STRANDEDNESS: UNKNOWN
                (D) TOPOLOGY: UNKNOWN (ii) MOLECULE TYPE: PEPTIDE (iii) HYPOTHETICAL: NO (iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:
                (F) TISSUE TYPE:
                (G) CELL TYPE:
                (H) CELL LINE:
                (I) ORGANELLE:

(vii) IMMEDIATE SOURCE:
                (A) LIBRARY:
                (B) CLONE:

(viii) POSITION IN GENOME:
                (A) CHROMOSOME/SEGMENT:
                (B) MAP POSITION:
                (C) UNITS:

(ix) FEATURE:
                (A) NAME/KEY:
                (B) LOCATION:
                (C) IDENTIFICATION METHOD:
                (D) OTHER INFORMATION:

(x) PUBLICATION INFORMATION:
                (A) AUTHORS:
                (B) TITLE:
                (C) JOURNAL:
                (D) VOLUME:
                (E) ISSUE:
                (F) PAGES:
                (G) DATE:
                (H) DOCUMENT NUMBER:
                (I) FILING DATE:
                (J) PUBLICATION DATE:
                (K) RELEVANT RESIDUES IN SEQ ID NO:

(ix) SEQUENCE DESCRIPTION: SEQ ID NO: 7:

Gly Ala Met Arg Val Thr Lys Asp Thr Asn Asp Asn Asn Leu Tyr
 1           5                  10                  15

(2) INFORMATION FOR SEQ ID NO: 8:

(i) SEQUENCE CHARACTERISTICS:
                (A) LENGTH: 30
                (B) TYPE: NUCLEIC ACID
                (C) STRANDEDNESS: UNKNOWN
                (D) TOPOLOGY: UNKNOWN (ii) MOLECULE TYPE:

(iii) HYPOTHETICAL: NO (iv) ANTI-SENSE:

(v) FRAGMENT TYPE:

(vi) ORIGINAL SOURCE:
                (A) ORGANISM:
                (B) STRAIN:
                (C) INDIVIDUAL ISOLATE:
                (D) DEVELOPMENTAL STAGE:
                (E) HAPLOTYPE:

( F ) TISSUE TYPE:
                        ( G ) CELL TYPE:
                        ( H ) CELL LINE:
                        ( I ) ORGANELLE:

( v i i ) IMMEDIATE SOURCE:
                        ( A ) LIBRARY:
                        ( B ) CLONE:

( v i i i ) POSITION IN GENOME:
                        ( A ) CHROMOSOME/SEGMENT:
                        ( B ) MAP POSITION:
                        ( C ) UNITS:

( i x ) FEATURE:
                        ( A ) NAME/KEY:
                        ( B ) LOCATION:
                        ( C ) IDENTIFICATION METHOD:
                        ( D ) OTHER INFORMATION:

( x ) PUBLICATION INFORMATION:
                        ( A ) AUTHORS:
                        ( B ) TITLE:
                        ( C ) JOURNAL:
                        ( D ) VOLUME:
                        ( E ) ISSUE:
                        ( F ) PAGES:
                        ( G ) DATE:
                        ( H ) DOCUMENT NUMBER:
                        ( I ) FILING DATE:
                        ( J ) PUBLICATION DATE:
                        ( K ) RELEVANT RESIDUES IN SEQ ID NO:

( i x ) SEQUENCE DESCRIPTION: SEQ ID NO: 8:

C T C A C T G G A T    G G T G G G A A G A    T G G A T A C A G T                                                     3 0

( 2 ) INFORMATION FOR SEQ ID NO: 9:

( i ) SEQUENCE CHARACTERISTICS:
                        ( A ) LENGTH: 19
                        ( B ) TYPE: NUCLEIC ACID
                        ( C ) STRANDEDNESS: UNKNOWN
                        ( D ) TOPOLOGY: UNKNOWN ( i i ) MOLECULE TYPE:

( i i i ) HYPOTHETICAL: NO ( i v ) ANTI-SENSE:

( v ) FRAGMENT TYPE:

( v i ) ORIGINAL SOURCE:
                        ( A ) ORGANISM:
                        ( B ) STRAIN:
                        ( C ) INDIVIDUAL ISOLATE:
                        ( D ) DEVELOPMENTAL STAGE:
                        ( E ) HAPLOTYPE:
                        ( F ) TISSUE TYPE:
                        ( G ) CELL TYPE:
                        ( H ) CELL LINE:
                        ( I ) ORGANELLE:

( v i i ) IMMEDIATE SOURCE:
                        ( A ) LIBRARY:
                        ( B ) CLONE:

( v i i i ) POSITION IN GENOME:
                        ( A ) CHROMOSOME/SEGMENT:
                        ( B ) MAP POSITION:
                        ( C ) UNITS:

( i x ) FEATURE:
                        ( A ) NAME/KEY:
                        ( B ) LOCATION:
                        ( C ) IDENTIFICATION METHOD:
                        ( D ) OTHER INFORMATION:

-continued ( x ) PUBLICATION INFORMATION:
     ( A ) AUTHORS:
     ( B ) TITLE:
     ( C ) JOURNAL:
     ( D ) VOLUME:
     ( E ) ISSUE:
     ( F ) PAGES:
     ( G ) DATE:
     ( H ) DOCUMENT NUMBER:
     ( I ) FILING DATE:
     ( J ) PUBLICATION DATE:
     ( K ) RELEVANT RESIDUES IN SEQ ID NO:

( i x ) SEQUENCE DESCRIPTION: SEQ ID NO: 9:

CAGGGGCCAG TGGATAGAC                                    1 9

( 2 ) INFORMATION FOR SEQ ID NO: 10:

( i ) SEQUENCE CHARACTERISTICS:
     ( A ) LENGTH: 3
     ( B ) TYPE: AMINO ACID
     ( C ) STRANDEDNESS: UNKNOWN
     ( D ) TOPOLOGY: UNKNOWN ( i i ) MOLECULE TYPE: PEPTIDE ( i i i ) HYPOTHETICAL: NO ( i v ) ANTI-SENSE:

( v ) FRAGMENT TYPE:

( v i ) ORIGINAL SOURCE:
     ( A ) ORGANISM:
     ( B ) STRAIN:
     ( C ) INDIVIDUAL ISOLATE:
     ( D ) DEVELOPMENTAL STAGE:
     ( E ) HAPLOTYPE:
     ( F ) TISSUE TYPE:
     ( G ) CELL TYPE:
     ( H ) CELL LINE:
     ( I ) ORGANELLE:

( v i i ) IMMEDIATE SOURCE:
     ( A ) LIBRARY:
     ( B ) CLONE:

( v i i i ) POSITION IN GENOME:
     ( A ) CHROMOSOME/SEGMENT:
     ( B ) MAP POSITION:
     ( C ) UNITS:

( i x ) FEATURE:
     ( A ) NAME/KEY:
     ( B ) LOCATION:
     ( C ) IDENTIFICATION METHOD:
     ( D ) OTHER INFORMATION:

( x ) PUBLICATION INFORMATION:
     ( A ) AUTHORS:
     ( B ) TITLE:
     ( C ) JOURNAL:
     ( D ) VOLUME:
     ( E ) ISSUE:
     ( F ) PAGES:
     ( G ) DATE:
     ( H ) DOCUMENT NUMBER:
     ( I ) FILING DATE:
     ( J ) PUBLICATION DATE:
     ( K ) RELEVANT RESIDUES IN SEQ ID NO:

( i x ) SEQUENCE DESCRIPTION: SEQ ID NO: 10:

Glu Lys Tyr
 1

( 2 ) INFORMATION FOR SEQ ID NO: 11:

```
        ( i ) SEQUENCE CHARACTERISTICS:
                ( A ) LENGTH: 11
                ( B ) TYPE: AMINO ACID
                ( C ) STRANDEDNESS: UNKNOWN
                ( D ) TOPOLOGY: UNKNOWN ( i i ) MOLECULE TYPE: PEPTIDE ( i i i ) HYPOTHETICAL:

( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:
                ( A ) LIBRARY:
                ( B ) CLONE:

( v i i i ) POSITION IN GENOME:
                ( A ) CHROMOSOME/SEGMENT:
                ( B ) MAP POSITION:
                ( C ) UNITS:

( i x ) FEATURE:
                ( A ) NAME/KEY:
                ( B ) LOCATION:
                ( C ) IDENTIFICATION METHOD:
                ( D ) OTHER INFORMATION:

( x ) PUBLICATION INFORMATION:
                ( A ) AUTHORS:
                ( B ) TITLE:
                ( C ) JOURNAL:
                ( D ) VOLUME:
                ( E ) ISSUE:
                ( F ) PAGES:
                ( G ) DATE:
                ( H ) DOCUMENT NUMBER:
                ( I ) FILING DATE:
                ( J ) PUBLICATION DATE:
                ( K ) RELEVANT RESIDUES IN SEQ ID NO:

( i x ) SEQUENCE DESCRIPTION: SEQ ID NO: 11:

Cys  Thr  Thr  Pro  Ala  Gln  Gly  Asn  Ser  Met  Phe
  1                   5                        1 0

( 2 ) INFORMATION FOR SEQ ID NO: 12:

( i ) SEQUENCE CHARACTERISTICS:
                ( A ) LENGTH: 12
                ( B ) TYPE: AMINO ACID
                ( C ) STRANDEDNESS: UNKNOWN
                ( D ) TOPOLOGY: UNKNOWN ( i i ) MOLECULE TYPE: PEPTIDE ( i i i ) HYPOTHETICAL: NO ( i v ) ANTI-SENSE:

( v ) FRAGMENT TYPE:

( v i ) ORIGINAL SOURCE:
                ( A ) ORGANISM:
                ( B ) STRAIN:
                ( C ) INDIVIDUAL ISOLATE:
```

( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( i x ) SEQUENCE DESCRIPTION: SEQ ID NO: 12:

Pro  Ser  Cys  Cys  Cys  Thr  Lys  Pro  Thr  Asp  Gly  Asn
 1              5                        1 0